United States Patent [19]

Shields et al.

[11] Patent Number: 5,543,317
[45] Date of Patent: Aug. 6, 1996

[54] MICROBIAL DEGRADATION OF TRICHLOROETHYLENE DICHLOROETHYLENES AND AROMATIC POLLUTANTS

[76] Inventors: Malcolm S. Shields, 1504 El Rito Dr., Gulf Breeze, Fla. 32561; Stephen C. Francesconi, 4486 Whisper Dr., Pensacola, Fla. 32504

[21] Appl. No.: 319,387

[22] Filed: Oct. 6, 1994

Related U.S. Application Data

[63] Continuation-in-part of Ser. No. 167,457, Dec. 15, 1993, abandoned, which is a continuation of Ser. No. 694,718, May 2, 1991, abandoned.

[51] Int. Cl.$^6$ ............................. C12N 1/21; C12N 1/14; C12N 5/10; C12N 15/53
[52] U.S. Cl. ................... 435/240.2; 435/252.3; 435/254.11; 435/262.5; 536/23.2
[58] Field of Search ................... 536/23.2, 23.7; 435/240.2, 252.3

[56] References Cited

U.S. PATENT DOCUMENTS 5,171,684  12/1992  Yen et al. ..................... 435/252.3

OTHER PUBLICATIONS

Shields et al., Appl. Env. Microbiol. 61:1352–1356 (1995).

*Primary Examiner*—Robert A. Wax
*Assistant Examiner*—Eric Grimes
*Attorney, Agent, or Firm*—Saliwanchik & Saliwanchik

[57] ABSTRACT

A novel bacterium named *Pseudomonas cepacia* PR1$_{23}$ (formerly designated G4 5223 PR1) has the desirable property of constitutively degrading hazardous chemicals, for example trichloroethylene, 1,1-dichloroethylene, cis-1,2 dichloroethylene, trans-1,2-dichloroethylene, toluene, phenol, o-cresol, m-cresol, o-xylene, and benzene, to harmless chemical entities. This microbe, and mutants thereof which retain the constitutive degradation property of the parent, can be used in bioreactor and in situ processes for degrading hazardous chemical compounds. The nucleic acid sequences which encode the degradative peptides have also been isolated and sequenced. Cells transformed with the isolated nucleic acid also produce the peptides comprising the enzyme which can constitutively degrade these hazardous chemicals. The enzyme can be isolated from such microorganisms (those which naturally harbor the gene or those which are transformed with the gene) and applied to a sample having the hazardous chemical(s) or contaminant(s) in order to degrade the contaminant(s).

3 Claims, 6 Drawing Sheets

MICROBIAL DEGRADATION OF TRICHLOROETHYLENE DICHLOROETHYLENES AND AROMATIC POLLUTANTS

CROSS-REFERENCE TO A RELATED APPLICATION

This is a continuation-in-part of application Ser. No. 08/167,457, filed Dec. 15, 1993 now abandoned; which is a continuation of application Ser. No. 07/694,718, filed May 2, 1991, now abandoned.

BACKGROUND OF THE INVENTION

Groundwater contamination by organic pollutants is a subject of major concern in the United States and, increasingly, the rest of the industrialized world. The sources of pollution are almost as numerous as the types of pollutants found. Sources range from agricultural uses, injection wells, underground storage tanks and hazardous waste sites, to illegal dumping in localities with no prior history of toxic chemical exposure. In monitoring chemical waste disposal sites within the United States, pollutants have been categorized according to the frequency of detection of certain chemical classes and specific chemicals within that class. The priority pollutants are divided into volatiles, acid extractables, pesticides and base/neutrals. Volatiles are the most frequently detected group, owing largely to their widespread use as solvents. The most often encountered components of these volatile chemical pollutants in 1986 were, in order of frequency, trichloroethylene, tetrachloroethylene, trans-1, 2-dichloroethylene, 1,1-dichloroethylene, (ranked first, second, third and fifth respectively of all volatiles detected (Rajagopal, R. (1986) *Environ. Prof.* 8:244–264). The most prevalent of these, trichloroethylene (TCE), has been in use since the 1940's, and the subject of environmental and human health concerns since its discovery in a contaminated aquifer in 1979 (Muntner, J. E., S. P. Devries (1987) *Toxics Law Reporter*, Jan. 14:874).

All reports of TCE transformation by anaerobic bacteria indicate a very slow process. The rapid mineralization of TCE by aerobic bacteria has been demonstrated for several microbial isolates. All require the addition of exogenous chemicals to induce production of the requisite TCE degrading enzymes. Toluene serves to induce oxygenase enzymes of *Pseudomonas putida* F1 (Nelson, M. J. K., S. O. Montgomery, P. H. Pritchard (1988) *App. Environ. Microbiol.* 54:604–606) and P. cepacia G4 (Nelson, M. J. K., S. O. Montgomery, E. J. O'Neill, P. H. Pritchard (1986) *Appl. Environ. Microbiol.* 42:383–384). These enzymes are in turn responsible for TCE degradation by these bacteria. The route of toluene catabolism by *P. cepacia* G4 has been shown to proceed via a monooxygenation pathway that results first in an ortho-hydroxylation of toluene (catalyzed by o-toluene monooxygenase) and subsequently a second hydroxylation ortho to the first hydroxyl to form 3-methylcatechol (Shields, M.S., S.O. Montgomery, P. J. Chapman, S. M. Cuskey, P. H. Pritchard (1989) *Appl. Environ. Microbiol.* 55:1624–1629).

Several U.S. patents have issued concerning bioremediation, usually employing microorganisms in conjunction with exogenous chemicals as inducers. Microorganisms which require induction prior to gaining the capability of degrading certain compounds are, by definition, non-constitutive. Examples of these patents include U.S. Pat. Nos. 4,452,894; 4,477,570; 4,664,805; 4,713,343; 4,749,491; 4,853,334; 4,859,594; 4,925,802; and 4,954,258.

U.S. Pat. No. 4,452,894 concerns a pure culture of a *Pseudomonas spp.* that can utilize a variety of chlorinated aromatic chemicals as sole sources of carbon.

U.S. Pat. No. 4,477,570 concerns the isolation of bacterial strains, specifically *Pseudomonas cepacia* var. niagarous, that degrade aromatic and halogenated aromatic chemicals.

U.S. Pat. No. 4,664,805 concerns a method for degradation of halogenated organic pollutants through the addition of non-toxic chemical analogs with or without non-indigenous microorganisms.

U.S. Pat. No. 4,713,343 concerns bacteria which utilize lower alkane gases as carbon sources and which are induced to degrade certain chloroethanes and chloroethenes after exposure to lower alkane gases.

U.S. Pat. No. 4,749,491 concerns a method for stimulating indigenous bacteria to degrade chlorinated hydrocarbons through the addition of oxygen and propane or methane.

U.S. Pat. No. 4,853,334 concerns a loss of haloaliphatic hydrocarbons in the presence of a *Pseudomonas fluorescens*. However, the *P. fluorescens*, which is a completely different species than the subject bacteria, provide insufficient utilization of chloroaliphatics for purposes of bioremediation of contaminated environmental sites. *P. fluorescens* incubated with trichloroethylene (TCE) resulted in minimal loss of the TCE (approximately 2%) after 24 hours and resulted in a loss of less than 15% of the TCE after as much as five days.

U.S. Pat. No. 4,859,594 concerns degradation of certain organic chemicals by a variant of *Pseudomonas cepacia*. However, the *P. cepacia* described in this patent does not degrade trichloroethylene (TCE).

U.S. Pat. No. 4,925,802 concerns a method for stimulating biodegradation of halogenated aliphatic hydrocarbons. The method uses microbes and an inducer. Specifically exemplified is the non-constitutive microbe, *Pseudomonas cepacia* strain G4, which is the parent of the constitutive microbe strain of the subject invention.

U.S. Pat. No. 4,954,258 concerns the addition of alkanes or lower alkanols to methanotrophic bacteria for the degradation of TCE.

Current technology for the treatment of TCE-contaminated soil and water has relied primarily upon pump-and-treat systems whereby TCE is distilled away from the water under vacuum, or alternatively is air-stripped and transferred onto an adsorbent such as charcoal. Recent review articles on this subject strongly question whether this technology alone will ever be effective in the remediation of hazardous wastes like TCE, since even long term treatments have had only modest effects on pollutant concentrations (Travis, C. C., C. B. Doty (1990) *Environ. Sci. Technol.* 24:1464–1466). In either event, the result of currently employed treatments is simply the transfer of the pollutant to an adsorbent or to the atmosphere.

The capability to destroy the contaminant at the site represents significant environmental and economic benefits and fills the need for efficient bioremediation technologies. Major limitations to the bacterial systems described in the prior art for the bioremediation of TCE is that most degrade TCE fortuitously. That is to say, their ability to alter TCE is necessarily linked to the production of an enzyme that can accept TCE as a surrogate substrate, the native substrate being that which is used to induce the enzyme's synthesis. Due to this co-metabolic relationship, TCE cannot be degraded to any significant extent in the environment without the addition of an exogenous inducing substrate, because TCE does not itself induce the enzymes required for its own degradation. As a result, these prior art organisms are faced with the additional limitation of degrading TCE in the presence of the required cosubstrate that competes for the same active site on the induced enzyme. In addition, this also means that the organisms are not active beyond the environmental zone that can be controlled through the addition of effective concentrations of inducer. The active bacteria are effectively "tethered" to the inducing substrate. Both of these limitations have serious implications to the design of both environmental and bioreactor applications. In addition, the application of native inducing substrates such as toluene or phenol is not possible in the environment as they are themselves pollutants.

The use of the microbe of the subject invention, advantageously, does not have the problems associated with the use of prior art microbes to remediate sites contaminated with hazardous chemicals. Briefly, the microbe of the invention, *P. cepacia* strain $PR1_{23}$ (formerly designated G4 5223 PR1 or G4 5223 Phe1), is a bacterial isolate that can function over a wide range of environmental conditions without the need for an added chemical inducer; it has a very high likelihood of competitive maintenance among native bacteria over the course of a given treatment; and it has evolved to utilize and grow on many organic pollutants likely to be found at waste treatment sites. One particular advantage is its efficient and rapid degradation of TCE.

BRIEF SUMMARY OF THE INVENTION

The subject invention concerns the use of a novel bacterial strain to degrade TCE over a wide range of environmental parameters without the requirement for added chemical inducers.

More specifically, the subject invention concerns the use of the novel strain designated *Pseudomonas cepacia* strain $PR1_{23}$ to degrade hazardous chemicals, for example, trichloroethylene (TCE), cis-1,2-dichloroethylene, trans-1,2-dichloroethylene, 1,1-dichloroethylene, and aromatic chemicals, for example benzene, phenol, toluene, o-xylene, m-xylene, o-cresol, and m-cresol. The novel bacterium is fully capable of the complete removal of the aforementioned pollutants under a variety of conditions, without the need to artificially or externally influence existing conditions (i.e. induce the requisite enzymes). Without the need for exogenous chemical inducers, this novel bacterium is an attractive biodegradative agent for remediation of TCE pollution for two reasons. First, and most importantly, the organism is free of the requirement of inducer and capable of functioning under a diverse set of conditions. Second, this constitutive degrader does not require an inducer that is a co-substrate for the same enzyme required to degrade TCE; in effect, it is not subject to competitive inhibition. As such, it can be used in both in situ environmental and bioreactor remediation processes.

Further, the enzyme(s) responsible for the degradation of the hazardous chemical compounds can be recovered from the extracts of cultures of the novel bacterium and used to degrade hazardous chemical compounds by procedures well known in the art.

The subject invention also includes a heretofore unclescribed DNA sequence which includes gene(s) harbored by the novel bacterium that encode enzyme(s) capable of degrading the hazardous chemicals. The subject DNA sequence can be isolated from the parent bacterium by using well-known cloning techniques. The isolated gene(s) can be used to transform other microbes by use of well-known transfer and expression vectors. The transformed host can be used in the same manner as the parent microbe to degrade hazardous chemical compounds.

The DNA sequence encoding the toluene ortho-monooxygenase (Tom) enzyme is present on a large self-transmissible plasmid denoted pTOM, as described herein. The nucleotide sequences of the tom genes and the predicted amino acid sequence of the enzyme subunits are presented as SEQ ID NOS. 1–7.

This plasmid, or the genes encoded thereon, can be transferred to other bacteria which, in turn, become capable of the constitutive degradation of TCE. The successful transfer of $pTOM_{31c}$ from E. coli JM109 ($pTOM_{31c}$) to two new bacterial strains (*Pseudomonas sp.* JS150, and *Pseudomonas cepacia* 17616) and their constitutive expression of the toluene ortho-monooxygenase have been confirmed. Similar transfers of the constitutive TCE degradative capability to other bacteria, chosen according to the specific biological demands of a particular site of TCE remedial action can also be made using methods and techniques which are readily available in the art.

Given the sequence data, fragments of this monooxygenase can be cloned. Such clones can form hybrid enzymes through novel subunit combinations with other multisubunit oxygenases. In addition, the sites of substrate catalysis can be examined based on the availability of the sequence information. This can be utilized, for example, in specific substitution strategies for key amino acids that alter the substrate binding and catalysis characteristics of the oxygenase.

BRIEF DESCRIPTION OF THE SEQUENCES

Figure 1:
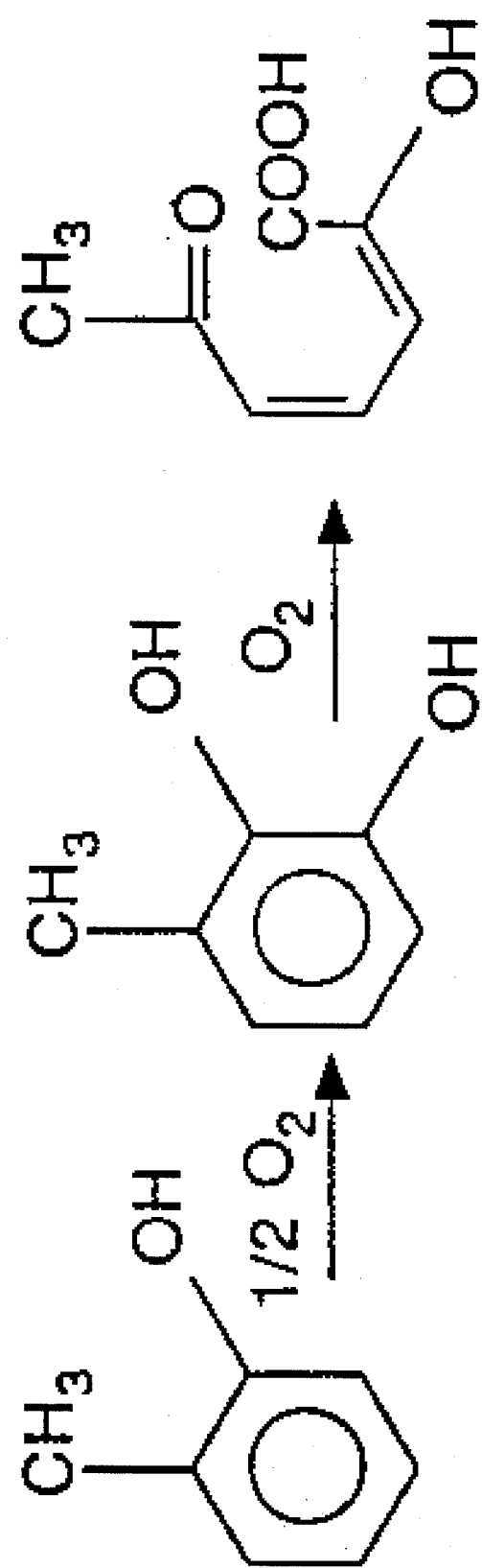
FIG. 1 illustrates the first two oxidations of toluene performed by *P. cepacia* G4.

SEQ ID NO. 1 shows the DNA sequence which includes the genes encoding toluene ortho-monooxygenase, designated tom.

SEQ ID NO. 2 shows the amino acid sequence encoded by the gene designated romA1. The open reading frame is between bases 2872–3068, inclusive, of SEQ ID NO. 1.

SEQ ID NO. 3 shows the amino acid sequence encoded by the gene designated tomA2. The open reading frame is between bases 3900–4176, inclusive, of SEQ ID NO. 1.

SEQ ID NO. 4 shows the amino acid sequence encoded by the gene designated tomA3. The open reading frame is between bases 4200–5760, inclusive, of SEQ ID NO. 1.

SEQ ID NO. 5 shows the amino acid sequence encoded by the gene designated tomA4. The open reading frame is between bases 5757–6114, inclusive, of SEQ ID NO. 1.

SEQ ID NO. 6 shows the amino acid sequence encoded by the gene designated tomA5. The open reading frame is between bases 6193–7252, inclusive, of SEQ ID NO. 1.

SEQ ID NO. 7 shows the amino acid sequence containing obvious homology with a known protein designated tomA0. The DNA encoding this open reading frame is between bases 2647 and 2759, inclusive.

DETAILED DISCLOSURE OF THE INVENTION

Upon contact with a culture of *Pseudomonas cepacia* strain $PR1_{23}$ (formerly designated G4 5223 PR1 or G4 5223 Phe1), or a mutant thereof which retains substantially the degradative capability of the parent bacterium, with a hazardous chemical, as defined herein, the hazardous chemical is degraded to a non-hazardous entity.

A subculture of *P. cepacia* strain $PR1_{23}$ has been deposited in the permanent collection of the Agricultural Research Service Culture Collection, Peoria, Ill. The accession number is as follows:

| Strain | Accession Number |
| --- | --- |
| *Pseudomonas cepacia* strain G4 5223 Phe1 | NRRL B-18811 |

For purposes of consistency, the deposited strain is referred to herein, under the current nomenclature, as *Pseudomonas cepacia* strain $PR1_{23}$. The subject culture has been deposited under conditions that assure that access to the culture will be available during the pendency of this patent application to one determined by the Commissioner of Patents and Trademarks to be entitled thereto under 37 CFR 1.14 and 35 U.S.C. 122. The deposit is available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposit will be stored and made available to the public in accord with the provisions of the Budapest Treaty for the Deposit of Microorganisms, i.e., it will be stored with all the care necessary to keep it viable and uncontaminated for a period of at least five years after the most recent request for the furnishing of a sample of the deposit, and in any case, for a period of at least thirty (30) years after the date of deposit or for the enforceable life of any patent which may issue disclosing the culture. The depositor acknowledges the duty to replace the deposit should the depository be unable to furnish a sample when requested, due to the condition of the deposit. All restrictions on the availability to the public of the subject culture deposit will be irrevocably removed upon the granting of a patent disclosing it.

The taxonomy of *Pseudomonas cepacia* strain $PR1_{23}$ is as follows:

*Pseudomonas cepacia* $PR1_{23}$ is an oxidase-positive and catalase-positive gram-negative obligately aerobic rod. It reduces nitrate to nitrite, is incapable of denitrification, and is unable to ferment glucose or hydrolyze esculin. Tests for urease, gelatinase, and arginine dihydrolase activity were negative. Beta-galactosidase activity is present and substrate utilization tests showed growth on D-glucose, D-arabinose, D-mannose, mannitol, N-acetyl-D-glucosamine, maltose, gluconate, caprate, adipate, citrate, and phenylacetate. L-malate is not utilized. Neither pyocyanin or fluorescein pigments are formed on selective media (King, E. O., M. K. Ward, D. E. Raney (1954)J. Lab. Clin. Med. 44:301). *Pseudomonas cepacia* $PR1_{23}$ is resistant to kanamycin sulfate (50µg/ml) in basal salts medium (Hareland, W., R. L. Crawford, P. J. Chapman, S. Dagley (1975) *J. Bacteriol* 121:272–285) containing 20 mM sodium lactate as the sole carbon source and is also capable of growth with penicillin G (5 mg/ml) as the sole carbon source. In addition, its demonstrated ability to store excess carbon as a microbial polyhydroxyalkanoate polyester may offer an excellent method to prolong degradative functions under the most extreme conditions.

The procedure of application of *P. cepacia* $PR1_{23}$ to the remediation of TCE-contaminated materials may be carried out through the use of various known procedures. For example, the organism can be used in a bioreactor (fixed film, fluidized bed, etc.) as well as in situ by methods generally such as those disclosed in U.S. Pat. Nos. 4,749,491 and 4,588,506, which are incorporated herein by reference.

Enzyme(s) produced by the novel microbe of the invention can be recovered from the cultured cells of the microbe. The recovery process can be one in which the microbial cells at harvest are extracted and the enzyme(s) recovered by standard procedures. The resulting enzyme preparation can be used to degrade hazardous chemicals, as disclosed herein. The treatment of hazardous chemicals with an enzyme preparation, as disclosed above, can be by use of columns and other means well known in the enzyme art. The enzyme preparation so used can be in either a crude or essentially pure form.

Enzymes of the subject invention constitutively degrade TCE. Because they can cooxidatively transform toluene (as a toluene ortho-monooxygenase), they have been designated "Tom." The genes encoding the Tom pathway enzymes, e.g., the TomA enzyme, are located on a native 108 kb plasmid ($pTom_{23c}$) in the subject *P. cepacia* $PR1_{23}$ strain. See Example 8, below. Novel recombinant microbes can be made by isolating the gene(s) from *P. cepacia* strain $PR1_{23}$ and transforming suitable hosts with the gene(s). These methods of transferring a gene to a suitable host are well known in the art and include using recombinant transfer vectors or plasmids in transformation, transfection, or conjugation techniques. The gene(s) encode enzymes which are capable of degrading hazardous chemical compounds.

The pTom plasmid has been isolated, and the DNA sequence comprising the gene(s) encoding the Tom enzymes has been determined. The DNA sequence comprising the TCE degradative gene region in *P. cepacia* $PR1_{23}$ is shown in SEQ ID NO. 1. This sequence has been cloned into *E. coli* and shown to confer to *E. coli* the ability to degrade TCE, toluene, and phenol. In this sequence are six open reading frames defining six subunits that appear to belong to a family of monooxygenases. The amino acid sequences encoded by these six reading frames are shown in SEQ ID NOS. 2–7.

The gene(s) required for constitutive TCE degradation which reside on the self-transmissible 108 kb plasmid in the *Pseudomonas cepacia* $PR1_{23}$ and the 114 kb plasmid in the $PR1_{31}$ strain have been demonstrated to be transmissible to and expressible in other bacteria. Advantageously, other bacteria can be thus genetically altered in many situations to constitutively degrade TCE, including bacteria suitable for bioreactors, or bacteria already present and functioning in TCE-contaminated environments. The following table shows the results of transfers of the native plasmid, pTom, and the two constitutive derivatives, pTom$_{23c}$ and pTom$_{31c}$, from their respective donors to a recipient strain to produce three transconjugant strains.

A wide variety of ways are available for introducing a gene into a microorganism host under conditions which allow for stable maintenance and expression of the gene. One can provide for DNA constructs which include the transcriptional and translational regulatory signals for expression of the gene, the gene under their regulatory control and a DNA sequence homologous with a sequence in the host organism, whereby integration will occur, and/or a replication system which is functional in the host, whereby integration or stable maintenance will occur.

Various manipulations may be employed for enhancing the expression of the messenger RNA, particularly by using an active promoter, as well as by employing sequences, which enhance the stability of the messenger RNA. The transcriptional and translational termination region will involve stop codon(s), a terminator region, and optionally, a polyadenylation signal.

In the direction of transcription, namely in the 5' to 3' direction of the coding or sense sequence, the construct will involve the transcriptional regulatory region, if any, and the promoter, where the regulatory region may be either 5' or 3' of the promoter, the ribosomal binding site, the initiation codon, the structural gene having an open reading frame in phase with the initiation codon, the stop codon(s), the polyadenylation signal sequence, if any, and the terminator region. This sequence as a double strand may be used by itself for transformation of a microorganism host, but will usually be included with a DNA sequence involving a marker, where the second DNA sequence may be joined to the expression construct during introduction of the DNA into the host.

A marker structural gene is used to provide for the selection of the host microbe which has acquired the desired nucleotide sequence (via, for example, transformation, electroporation, conjugation, or phage mediated). The marker will normally provide for selective advantage, for example, providing for biocide resistance, e.g., resistance to antibiotics or heavy metals; complementation, so as to provide prototrophy to an auxotrophic host, or the like. Preferably, complementation is employed, so that the modified host may not only be selected, but may also be competitive in the field. One or more markers may be employed in the development of the constructs, as well as for modifying the host. The organisms may be further modified by providing for a competitive advantage against other wild-type microorganisms in the field. For example, genes expressing metal chelating agents, e.g., siderophores, may be introduced into the host along with the structural gene. In this manner, the enhanced expression of a siderophore may provide for a competitive advantage for the host, so that it may effectively compete with wild-type microorganisms.

Where no functional replication system is present, the construct will also include a sequence of at least 50 basepairs (bp), preferably at least about 100 bp, and usually not more than about 1000 bp of a sequence homologous with a sequence in the host. In this way, the probability of legitimate recombination is enhanced, so that the gene will be integrated into the host and stably maintained by the host. Desirably, the gene will be in close proximity to the gene providing for complementation as well as the gene providing for the competitive advantage. Therefore, in the event that a gene is lost, the resulting organism will be likely to also lose the complementing gene and/or the gene providing for the competitive advantage, so that it will be unable to compete in the environment with the organism retaining the intact construct.

A large number of transcriptional regulatory regions are available from a wide variety of microorganism hosts, such as bacteria, bacteriophage, cyanobacteria, algae, fungi, and the like. Various transcriptional regulatory regions include the regions associated with the trp gene, lac gene, gal gene, the lambda left and right promoters, the Tac promoter, the naturally-occurring promoters associated with the gene, where functional in the host. The termination region can be the termination region normally associated with the transcriptional termination region or a different transcriptional termination region, so long as the two regions are compatible and functional in the host.

Where stable episomal maintenance or integration is desired, a plasmid can be employed which has a replication system which is functional in the host. The replication system may be derived from the chromosome, an episomal element normally present in the host or a different host, or a replication system from a virus which is stable in the host.

The gene can be introduced between the transcriptional and translational initiation region and the transcriptional and translational termination region, so as to be under the regulatory control of the initiation region. This construct will be included in a plasmid, which will include at least one replication system, but may include more than one, where one replication system is employed for cloning during the development of the plasmid and the second replication system is necessary for functioning in the ultimate host. In addition, one or more markers may be present, which have been described previously. Where integration is desired, the plasmid will desirably include a sequence homologous with the host genome.

The transformants can be isolated in accordance with conventional ways, usually employing a selection technique, which allows for selection of the desired organism as against unmodified organisms or transferring organisms, when present. The transformants then can be tested for degrading hazardous chemical compounds.

Suitable host cells can be Gram-negative bacteria, including but not necessarily limited to, Enterobacteriaceae, e.g., Escherichia and other Pseudomonadaceae.

The recombinant cellular host containing the gene(s) may be grown in any convenient nutrient medium, where the DNA construct provides a selective advantage, providing for a selective medium so that substantially all or all of the cells retain the gene. These cells may then be harvested in accordance with conventional ways.

The genes and proteins useful according to the subject invention include not only the full length sequences disclosed but also fragments of these sequences, variants, mutants, and fusion proteins which retain the characteristic activity of the proteins specifically exemplified herein. As used herein, the terms "variants" or "variations" of genes refer to nucleotide sequences which code for the same proteins or which code for equivalent proteins having the same biological activity. As used herein, the term "equivalent proteins" refers to proteins having the same or essentially the same biological activity as the claimed proteins.

It should be apparent to a person skilled in this art that genes coding for active proteins and the proteins themselves can be identified and obtained through several means. The specific genes exemplified herein may be obtained from the isolates deposited at a culture depository as described above. These genes, or portions or variants thereof, may also be constructed synthetically, for example, by use of a gene synthesizer. Variations of genes may be readily constructed using standard techniques for making point mutations. Also, fragments of these genes can be made using commercially available exonucleases or endonucleases according to standard procedures. For example, enzymes such as Bal31 or site-directed mutagenesis can be used to systematically remove nucleotides from the ends of these genes. Also, genes which encode active fragments may be obtained using a variety of restriction enzymes. Proteases may be used to directly obtain active fragments of these proteins.

Fragments and equivalents which retain the biological activity of the exemplified proteins would be within the scope of the subject invention. Also, because of the redundancy of the genetic code, a variety of different DNA sequences can encode the amino acid sequences disclosed herein. It is well within the skill of a person trained in the art to create these alternative DNA sequences encoding the same, or essentially the same, proteins. These variant DNA sequences are within the scope of the subject invention. As used herein, reference to "essentially the same" sequence refers to sequences which have amino acid substitutions, deletions, additions, or insertions which do not materially affect biological activity. Fragments retaining biological activity are also included in this definition.

A further method for identifying the proteins and genes of the subject invention is through the use of oligonucleotide probes. These probes are nucleotide sequences having a means for detection. It is well recognized in the art that nucleic acid sequences can be labelled with a reporter molecule in order to visualize the sequence and facilitate the identification of other nucleic acid fragments to which it hybridizes. These labelling techniques are commonly known to and employed by ordinarily skilled artisans. As is well known in the art, if the probe molecule and nucleic acid sample hybridize by forming a strong bond between the two molecules, it can be reasonably assumed that the probe and sample have substantial homology. The probe's means of detection provides a means for determining in a known manner whether hybridization has occurred. Such a probe analysis provides a rapid method for identifying protein-encoding genes of the subject invention. The nucleotide segments which are used as probes according to the invention can be isolated from the organism's DNA as described herein or can be synthesized by use of DNA synthesizers using standard procedures. These nucleotide sequences can also be used as PCR primers to amplify genes of the subject invention.

It would be recognized in the art that the gene product can be used in standard antibody production procedures, for use as a molecular weight or size marker, and the like. Moreover, the gene product can be used to produce a transgenie protein useful for its activity as an enzyme catalyzing the conversion of a substrate to a new product. For example, the tom gene product can be used to convert TCE and related compounds to substances which are less hazardous to the environment. This nucleic acid sequence, and fragments thereof, can also be used as a probe to detect other nucleic acid sequences of interest.

Certain proteins of the subject invention have been specifically exemplified herein. Since these proteins are merely exemplary of the proteins of the subject invention, it should be readily apparent that the subject invention further comprises variant or equivalent proteins (and nucleotide sequences coding for equivalent proteins) having the same or essentially the same biological activity of the exemplified proteins. These equivalent proteins can have amino acid homology with an exemplified protein. This amino acid homology will typically be greater than 75%, preferably be greater than 90%, and most preferably be greater than 95%. The amino acid homology will be highest in certain critical regions of the protein which account for biological activity or are involved in the determination of three-dimensional configuration which ultimately is responsible for the biological activity. In this regard, certain amino acid substitutions are acceptable and can be expected if these substitutions are in regions which are not critical to activity or are conservative amino acid substitutions which do not affect the three-dimensional configuration of the molecule. For example, amino acids may be placed in the following classes: non-polar, uncharged polar, basic, and acidic. Conservative substitutions whereby an amino acid of one class is replaced with another amino acid of the same type fall within the scope of the subject invention so long as the substitution does not materially alter the biological activity of the compound. Table 1 provides a listing of examples of amino acids belonging to each class.

TABLE 1

| Class of Amino Acid | Examples of Amino Acids |
| --- | --- |
| Nonpolar | Ala, Val, Leu, Ile, Pro, Met, Phe, Trp |
| Uncharged Polar | Gly, Ser, Thr, Cys, Try, Asn, Gln |
| Acidic | Asp, Glu |
| Basic | Lys, Arg, His |

In some instances, non-conservative substitutions can also be made. The critical factor is that these substitutions must not significantly detract from the biological activity of the protein.

Following are examples which illustrate procedures, including the best mode, for practicing the invention. These examples should not be construed as limiting. All percentages are by weight and all solvent mixture proportions are by volume unless otherwise noted.

EXAMPLE 1

Aromatic Degradative Pathway of *P. cepacia* G4

The toluene catabolic pathway of *P. cepacia* G4 was established using mutants induced with nitrosoguanidine and heavy oxygen isotope incorporation into the catabolic products (Shields, M. S., S. O. Montgomery, P. J. Chapman, S. M. Cuskey, P. H. Pritchard (1989) *Appl. Environ. Microbiol.* 55:1624–1629). See FIG. 1.

Figure 2:
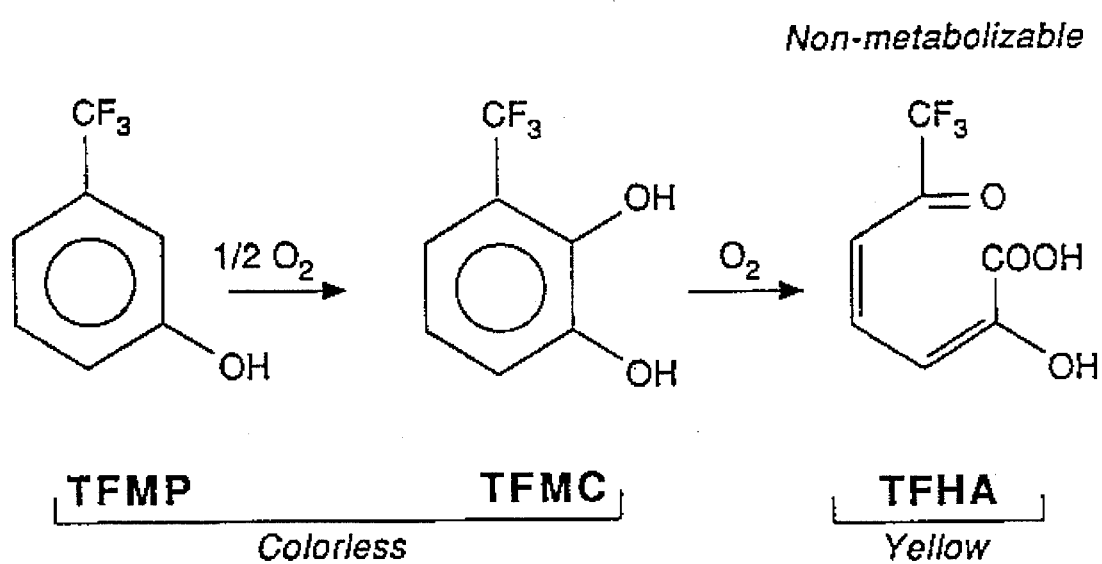
FIG. 2 is a presentation of the probable route of oxidation of the *m-cresol* analog: 3-trifluoromethylphenol (TFMP) to the yellow ring-cleavage product.

Mutants of this pathway were detectable in the presence of the fluorinated analog of m-cresol; m-trifluoromethylphenol (TFMP) (Aldrich Chemical Co., Milwaukee, Wis). Wild type cells were capable of the oxidation of TFMP to a bright yellow transformation product presumed to be 7,7,7-trifluoro-2-hydroxy-6-oxo-2,4-heptadienoic acid (Engesser, K. H., R. B. Cain, H. J. Knackmuss (1988) *Arch. Microbiol.* 149:188–197). Due to anticipated structural similarities between TFMP oxidation products and intermediates of the toluene pathway, it was predicted that mutants failing to produce yellow color with TFMP would lack either the cresol monooxidation or catechol dioxygenation functions. See FIG. 2.

Mutants were characterized according to their ability to grow with different aromatic substances and their reaction with TFMP as shown in Table 2.

TABLE 2

Mutant Phenotypes

| Strain | Genotype | TFMP Color Reaction[a] Induced with: | | Growth with: | | | |
|---|---|---|---|---|---|---|---|
| | | Tol[b] | Phe | Tol | Phe | o-Cre | m-Cre |
| G4 | wild type | + | + | + | + | + | + |
| G4 (100) | tomA | – | – | – | – | – | – |
| G4 (100R1) | tomA Revertant | + | + | + | + | + | + |
| G4 (102) | tomB | Br[c] | Br[c] | – | | +[d] | – |
| G4 (103) | tomC | Ye[c] | + | – | + | – | – |

[a]Conversion of 3-trifluoromethylphenol (TFMP) to its yellow ring cleavage product is indicated by "+."
[b]Toluene (Tol), phenol (Phe), o-cresol (o-Cre) and m-cresol (m-Cre).
[c]TFMP conversion was not detectable in colonies due to accumulation of either brown (Br) or yellow (Ye) colored products formed in the presence of inducer.
[d]Very slow growth (5–7 days for recognizable colonies).

These classes of mutants were further characterized and confirmed by examination of the effects of mutation on whole cell oxygen uptake in the presence of different substrates and by measurement of the specific activities of enzymes in cell free extracts as shown in Table 3.

TABLE 3

Cell free enzyme activities
Enzyme activities (nmol* $min^{-1}$ mg $protein^{-1}$)[a]

| Strain | Substrate | C230 | | Hydrolase | | Dehydrogenase |
|---|---|---|---|---|---|---|
| | | Cat | 3mCat | Hms | Hod | Hms |
| G4 | | 6550 | 3780 | 112 | 1860 | 52 |
| G4 (100) | | 5290 | 1970 | 195 | 683 | 122 |
| G4 (100R1) | | 3390 | 5900 | 281 | 871 | 86 |
| G4 (102) | | 0.3 | 0.6 | 148 | 563 | 74 |
| G4 (103) | | 1680 | 1210 | 0.2 | 0.5 | 34 |

[a]Enzyme activities are reported as the average of duplicate determinations of cell-free extracts obtained from cells induced with toluene.
[b]Abbreviations: C230, catechol-2,3-dioxygenase, Cat, catechol; 3mCat, 3-metylcathechol; Hms, hydroxymuconic semialdehyde; Hod, 2-hydroxy-6-ketohepta-2,4-dienoate.

Figure 3:
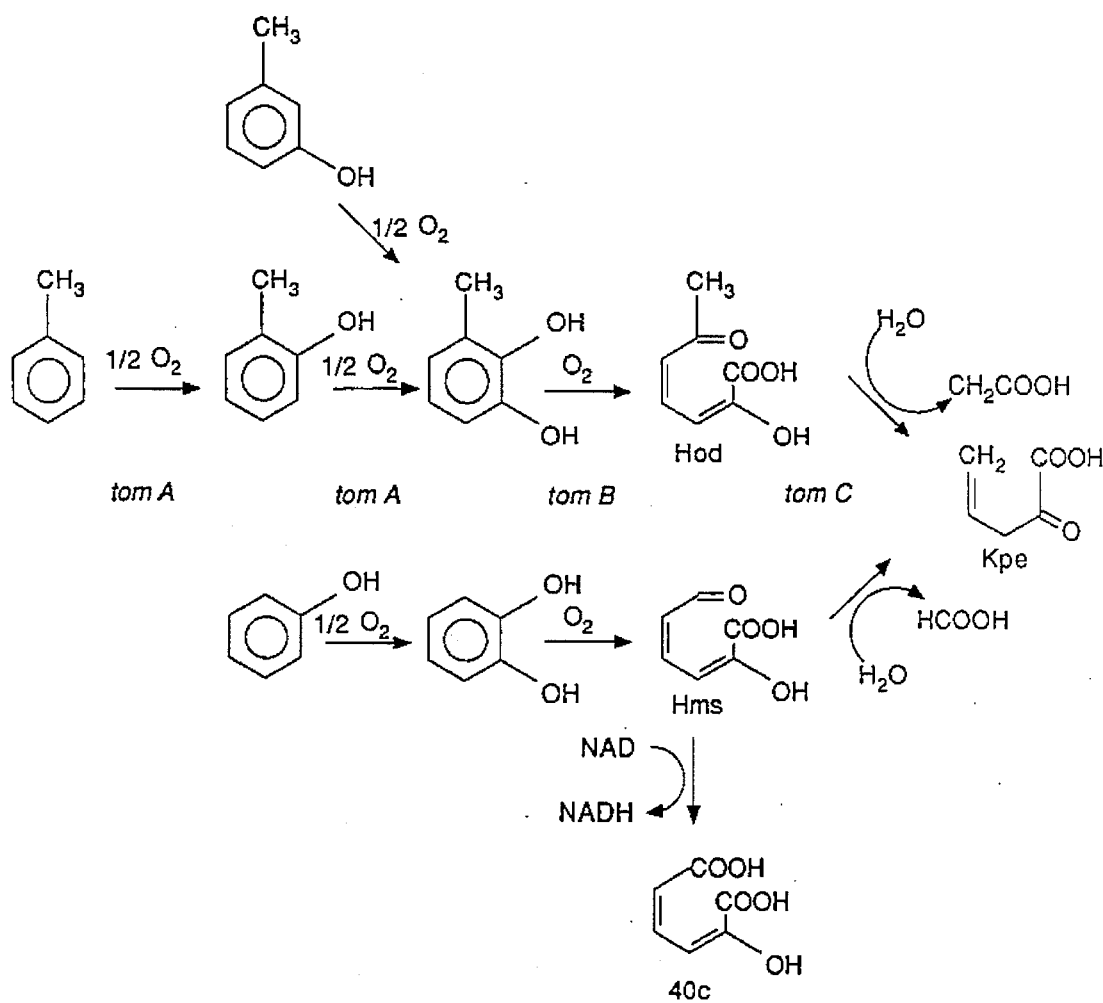
FIG. 3 is a portrayal of the known catabolic transformations associated with the initial enzymes of toluene catabolism in *P. cepacia* G4.
Figure 4A:
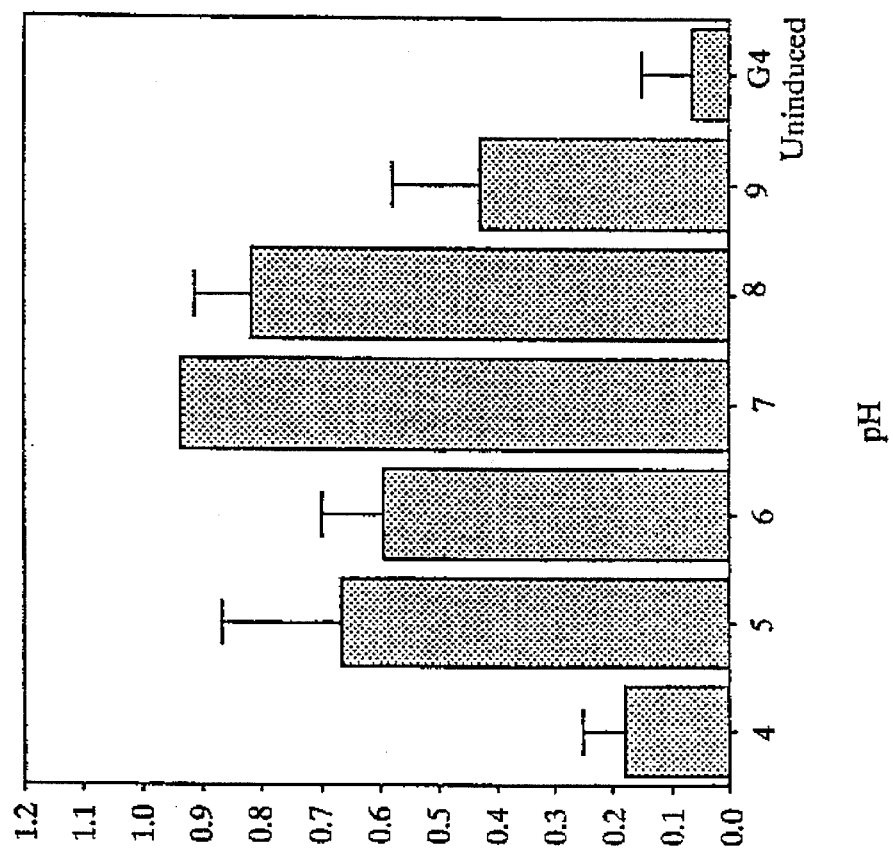
FIG. 4 shows the effects of several environmental variables on the initial (i.e., over the first 1–2 hr) rate of TCE degradation by *P. cepacia* G4 5223 are shown.
Figure 4B:
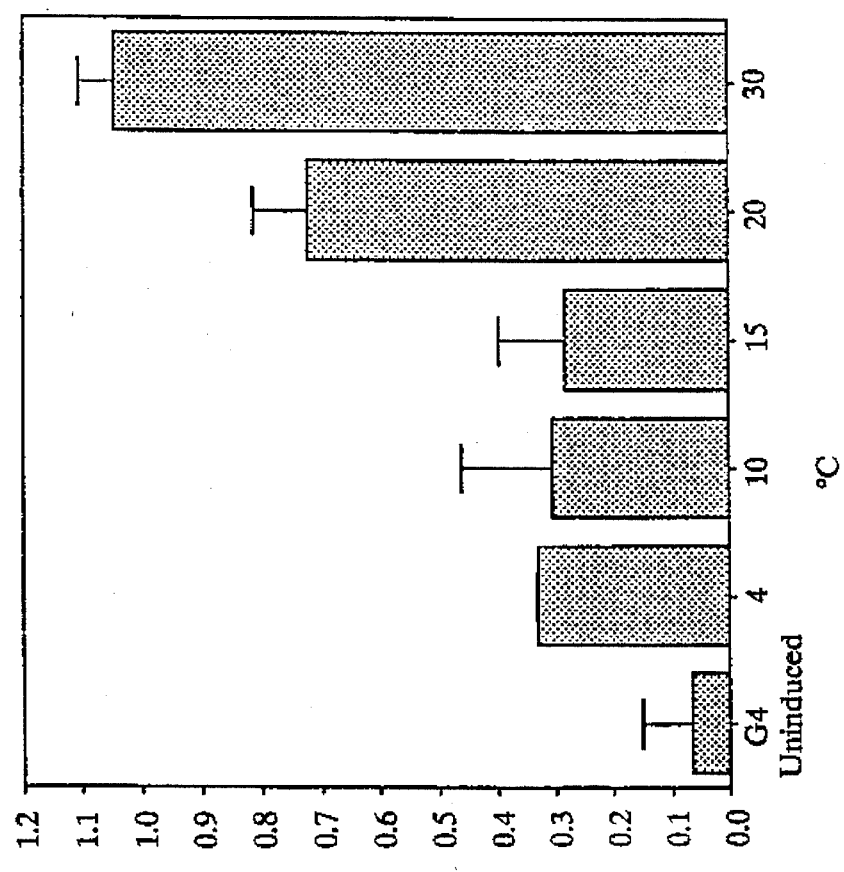
Figure 4C:
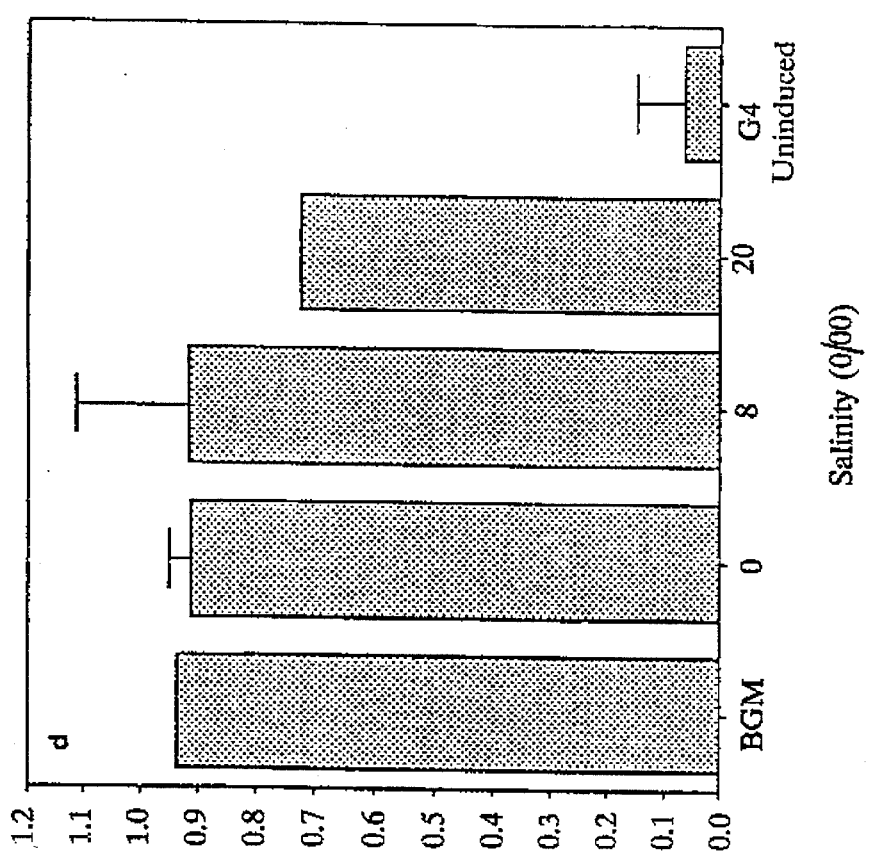
Figure 4D:
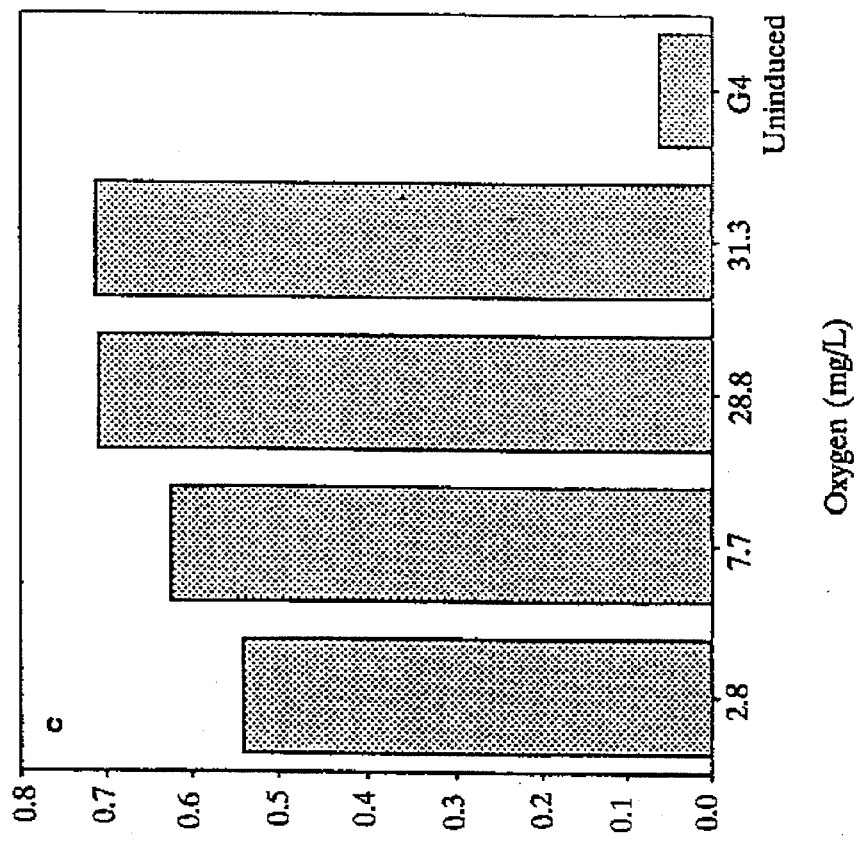

Enzyme activities were derived from lactate grown cells following 6 hours exposure to air-entrained toluene vapor. Cell free extracts were analyzed for catechol-2,3-dioxygenase (Gibson, D. T. (1971) In D. J. R. Norris and D. W. Ribbons, eds., *Methods in Microbiology*, Academic Press, New York, pp. 462–478), hydroxymuconic semialdehyde (Hms) hydrolase and Hms dehydrogenase activities (Bayly, R. C., G. J. Wigmore (1973) *J. Bacteriol.* 113:1112–1120). This allowed the summation of data into the form of this comprehensive aromatic pathway cluster of *P. cepacia* G4 as shown in FIG. 3.

EXAMPLE 2

Toluene o-Monooxygenase of *P. cepacia* G4 is Required for TCE Degradation

Cells representative of the different mutant classes were induced using toluene and analyzed for their ability to degrade TCE. See Table 4. Washed cells were resuspended in basal salts medium containing 20 μM TCE to a cell density that yielded an absorbance at 600 nm of 0.2. These samples were sealed in 10 ml glass vials with Teflon-lined rubber septa and crimp rings. These vials were incubated inverted at 24° C. overnight with rotary shaking (180 rpm). TCE was extracted by injection of two ml pentane (HPLC grade, Aldrich Chemical Co.) with rotary shaking in an upright position at 180 rpm, 24° C. for 30 minutes. The pentane phase was transferred to GC vials with Teflon liners and analyzed on an HP 5790 gas chromatograph equipped with an autosampler and electron capture detector. Separation was achieved with a Vocol capillary column, 30 m, 0.53 mm ID, fused silica, 3.0 μm film thickness (Supelco, Inc., Bellefonte, Pa. #2-5320) at 50° C.

Only the mutant impaired in its toluene monooxygenase activity (tomA) failed to degrade TCE. The spontaneous revertant of this mutant: strain G4 100R1 fully regained both its ability to express the toluene o-monooxygenase as well as degrade TCE.

TABLE 4

TCE degradation by cells induced with Phenol or Toluene

| | TCE remaining (μM)[a] | |
|---|---|---|
| Strain | Phe[b]-Induced | Tol-Induced |
| G4 | <0.02 | <0.02 |
| G4(100) | 3.67 (±0.03) | 3.56 (±0.46) |
| G4(100R1) | <0.02 | <0.02 |
| G4(102) | <0.02 | <0.02 |
| Uninoculated | 3.72 (±0.07) | |

[a]Means of triplicate TCE determinations (± standard deviation) after 24 h, using either toluene- (Tol) or phenol- (Phe) induced cultures.
[b]Phenol or toluene induction of G4 was accomplished by exposing an overnight 20 mM lactate culture to 2 mM phenol or toluene. Two hours later the cells were harvested by centrifugation, washed and exposed to TCE in sealed vials with air headspaces.

EXAMPLE 3

Isolation of a Tn5 Induced Toluene Monooxygenase Mutant of *P. cepacia* G4

A method was developed for the isolation of transposon induced tomA mutants. Transposon mutagenesis was carried by a triparental mating: *E. coli* JM109 (pRZ102) (Jorgemen, R. A., S. J. Rothstein, W. S. Reznikoff (1979) *Molec. Genet.* 177:65–72)×*E. coli* JM109 (pRK2013) (Figurski, D. H., D. R. Helinski (1979) *Proc. Natl. Acad. Sci. USA* 76:1648–1652)×*P. cepacia* G4. Selection for *P. cepacia* G4 containing a transposed copy of the transposon, Tn5, was accomplished by growth of the mating mixture on basal salts medium containing 20 mM sodium lactate and 50 μg/ml kanamycin sulfate. Exposure to toluene vapor induced the requisite enzymes for toluene catabolism.

Colonies were transferred from the surface of the plate to nitrocellulose filters (0.45 μm pore size, Schliecher and Schuell, Keene, N. H.) previously soaked in an aqueous solution of 5 mM TFMP and air dried. Mutants tomA and tomB (i.e. those lacking the toluene monooxygenase and catechol dioxygenase respectively) are easily differentiated as colorless colonies among a background of yellow wild type colonies. The two mutant types are readily distinguishable from one another as the catechol-2,3-dioxygenase mutant (tomB) turns brown in (>12 hr) basal salts media containing 20 mM sodium lactate and 2 mM phenol (due to the accumulation and subsequent auto-oxidation of catechol). Mutants lacking toluene monooxygenase (tomA) do not.

Incorporation of TFMP in solid media was not sufficient to determine a single colony response as the color development required several minutes over which time the yellow product diffused throughout the plate. The nitrocellulose membrane lift technique was developed in response to this limitation. Colonies transferred to its surface immediately begin desiccation. Any water soluble yellow product produced by that colony does not diffuse away. The result is a distinct yellow coloration of all colonies capable of transforming TFMP to the yellow product.

Using this technique the transposon mutant, P. cepacia G4 5223 was isolated. This mutant class (typified by G4 100) lacked the ability to transform TFMP and to degrade TCE.

EXAMPLE 4

Production of Constitutive Derivative Without Use of Tn5

A chemically induced mutant of pTOM in P. cepacia G4 and its spontaneous constitutive TCE-degradative derivative were obtained from P. cepacia G4 following nitrosoguanidine mutagenesis and selection with triphenyltetrazolium chloride and phenol. This is advantageous in that it is now demonstrated that a constitutive derivative can be produced without the need for mutagenesis with a transposon, e.g., Tn5. The presence of Tn5 has been known to cause environmental regulatory agencies to be reluctant to approving such altered organisms for use in the field. Thus, the absence of Tn5 can be advantageous in gaining regulatory approvals for these beneficial organisms. Appearance of constitutive expression was detected through reversion to phenol utilization and uninduced TFMP and TCE oxidation. The results are shown below in Table 5.

TABLE 5

Constitutive TCE degradative derivative from a nitrosoguanidine mutant of pTOM in P. cepacia G4

| Strain | Phenol Induced | TFMP | TCE Remaining[1] (µM) | % of Uninduced Parent Strain |
| --- | --- | --- | --- | --- |
| G4 (pTOM$_{301}$) | Yes | – | 9.70 | 97.88 |
| G4 (pTOM$_{301}$) | No | – | 9.71 | 97.88 |
| G4 (pTOM$_{301c}$) | Yes | + | 0.02 | 0.20 |
| G4 (pTOM$_{301c}$) | No | + | 0.03 | 0.30 |

[1]Following overnight sealed bottle degradation assay
Note: the constitutive strains are indicated by the subscript "c".

EXAMPLE 5

Procedure for Isolation and Characterization of a Constitutive TCE Degrader

Mutants of tomA (unable to use phenol) were inoculated by patching to basal salts plates containing 2 mM phenol as the sole carbon source. Rare colonies arising were picked to basal salts plates containing 20 mM sodium lactate as the sole carbon source. These colonies were in turn pulled to nitrocellulose discs impregnated with TFMP (Example 3) and compared to wild type P. cepacia G4 similarly grown on this non-inducing medium. Colonies that became yellow were chosen as potentially constitutive for tomA and tomb gene products. In this way P. cepacia strain PR1$_{23}$, PR1$_{31}$, and PR$_{301}$ were isolated.

The first strain was compared to the wild-type strain for its ability to constitutively degrade TCE. The results are shown in Table 6. In addition, Table 7 shows enzyme induction versus constitutivity for the P. cepacia strains G4, G4 5223, and PR1$_{23}$.

TABLE 6

TCE degradation without inducer

| Strain | TCE Remaining (µM[a]) |
| --- | --- |
| No cells added | 83.3 ± 7.6 |
| G4 5223 | 86.2 ± 3.1 |
| PR1$_{23}$ | 1.4 ± 1.4 |

[a]Mean TCE concentration of triplicate samples ± standard deviation after overnight incubation with the indicated strains (at a cell density equivalent to an $A_{600} = 0.2$).

TABLE 7

Enzyme induction vs. constitutivity

| | | Enzyme Activity nmoles min$^{-1}$ mg protein$^{-1}$ | | | |
| --- | --- | --- | --- | --- | --- |
| | Substrate | C230 | | Hms Hydrolase | |
| Strain | Inducer | Cat | 3mCat | Hms | Hod |
| PR1$_{23}$ | none | 156 | 50.4 | 0.44 | 2.5 |
| PR1$_{23}$ | phenol | 48 | 34.9 | 0.20 | 5.5 |
| G4 5223 | none | 0.07 | 2.2 | 0 | 5.5 |
| G4 5223 | phenol | 13.1 | 31.4 | 0 | 1.3 |
| G4 | none | 2.1 | 3.7 | 0 | 3.0 |
| G4 | phenol | 53.6 | 62.5 | 0.87 | 1.2 |

Abbreviations: C230, catechol-2,3-dioxygenase; Hms, hydroxymuconic semialdehyde; Cat, catechol; 3mCat, 3-methylcatechol; Hod, 2-hydroxy-6-oxohepta-2,4-dienoate.

The genetic stability of invention strain PR1$_{23}$ was assessed by growing the cells under non-selective (i.e. basal salts medium with sodium lactate at 20 mM as the sole carbon source) and under selective conditions (i.e. the same medium containing in addition 50 µg kanamycin sulphate/ml) through serially diluted batch cultures, allowing 10 generations per transfer. As shown in Table 8, below, following the accumulation of ca. 100 generations, the resulting population of cells was tested for kanamycin resistance (in the non-selective group) and the ability to constitutively transform TFMP to a yellow product (both groups):

TABLE 8

Genetic stability

| 100 Generation | CFU × 10$^8$ on Plates Containing: | |
| --- | --- | --- |
| Growth on: | Lactate | Lactate + Kanamycin |
| Lactate | 5.9 | 7.3 |
| Lactate + Kanamycin | 7.5 | 8.4 |

Lactate-grown colonies were picked to lactate plates containing 50 µg/ml kanamycin. Those from 100 generations without selection exhibited 100% kanamycin resistance (150/150) as did those taken from kanamycin growth selection (75/75).

All colonies maintained tomA constitutivity under either growth condition (as demonstrated by pulling colonies to TFMP-impregnated nitrocellulose).

EXAMPLE 6

TCE Degradation Under Ranges of Physical Conditions

In order to assess the capacity for P. cepacia PR1$_{23}$ to degrade TCE under anticipated ranges of environmental conditions the effects of oxygen concentration, pH, temperature and salinity were determined using a no air headspace TCE degradation assay (Folsom, B. R., P. J. Chapman, P. H. Pritchard (1990) *Appl. Environ. Microbiol.* 56:1279–1285) that mimicked a contaminated aquifer in that no gas headspaces were present. Unless otherwise noted in the salinity effect determinations, the liquid medium was the basal salts medium buffered with Tris-HCl rather than phosphate. The results are shown in FIGS. 4a, 4b, 4c and 4d.

EXAMPLE 7

Constitutive Degradation of 1,1-Dichloroethylene, cis-1,2-Dichloroethylene, and trans- 1,2-Dichloroethylene The range of chlorinated aliphatic substrates acted upon by *P. cepacia* $PR1_{23}$ was determined by the ability of cells to degrade 10 μM TCE, 1,1-dichloroethylene, cis-1,2-dichloroethylene, trans-1,2-dichloroethylene and tetrachloroethylene in 2 ml of basal salts medium without additional carbon sources in 10 ml Teflon lined vessels during an overnight incubation at 24° C. See Table 9. Triplicate samples were analyzed by gas chromatography for appearance of detectable products as well as disappearance of parent compounds:

TABLE 9

Chloroaliphatic substrates of *P. cepacia* $PR1_{23}$

| | % Chloroaliphatics Remaining[a] | | | | |
|---|---|---|---|---|---|
| | 1,1-DCE | cis-1,2-DCE | trans-1,2-DCE | TCE | PCE |
| Uninoculated | 100 | 100 | 100 | 100 | 100 |
| G4 Uninduced | 104 | 69 | 107 | 133 | 103 |
| $PR1_{23}$ Uninduced | 50 | 12.3[M] | ND[M] | 2.0 | 104 |

[a]Percent substrate remaining as compared to uninoculated controls, abbreviations: 1,1-DCE, 1,1-dichloroethylene; cis-1,2-DCE, cis-1,2-dichloroethylene; trans-1,2-DCE, trans-1,2-dichloroethylene; TCE, trichloroethylene; PCE, perchloroethylene; ND, Not Detectable. Starting concentration was 10 μM for all substrates.
[M]indicates that a metabolite was detected using gas chromatography.

EXAMPLE 8

Localization of Gene Encoding TCE Degradative Enzyme to a Plasmid

The previously described Tn5 mutagenesis yielded tomA mutants G4 5223 ($pTOM_{23}$) and G4 5231 ($pTOM_{31}$), which were unable to utilize phenol. These mutants spontaneously regained the ability to grow on phenol and, in so doing, became constitutive for tomA and tomb gene expression (Shields, M. S., M. J. Reagin (1992) *Appl. Environ. Microbiol.* 58:3977–3983). Preliminary evidence indicated a plasmid location of the tom operon. *Pseudomonas cepacia* G4 contains two detectable extrachromosomal elements of approximately 50 and 108 kb. $PR1_{23}$ was cured of the 108 kb plasmid. This cured strain ($PR1_{23}$Cure) was unable to grow on phenol and toluene. Such growth has been shown to require Tom. Transfer of the 108 kb plasmid (pTOM) from strain G4, which is inducible to Tom expression, to $PR1_{23}$Cure restored the ability to grow on toluene and phenol and resulted in the expression or Tom in an inducible manner. Transfer of $pTOM_{23c}$ from $PR1_{23}$ to a rifampicin and naladixic acid resistant derivative of $PR1_{23}$Cure reestablished phenol and toluene supported growth and resulted in expression of Tom in a constitutive manner. An 11.2 kb EcoRI restriction fragment of $pTOM_{23c}$ was cloned into pGEM4Z to produce a recombinant plasmid pMS64. Tom and catechol 2,3-dioxygenase (C23O ) activities were evident in *Escherichia coli* JM109 (pMS64) which oxidized TCE and produced o-cresol from toluene, 3-methylcatechol from m-cresol and o-cresol, catechol from phenol, and 2-hydroxymuconic semialdehyde from catechol. The 11.2 kb EcoRI fragment hybridized exclusively to pTOM in G4. These results show that the genes encoding Tom and C23O are located on an approximately 108 kb degradative plasmid of *P. cepacia* G4, designated pTOM.

Materials and Methods

Bacterial strains, plasmids, and media. *Pseudomonas cepacia* strains used in this study are listed in Table 10.

TABLE 10

Bacterial strains

| | Plasmid | Modification | Tom Phenotype |
|---|---|---|---|
| *P. cepacia* strain | | | |
| G4 | pTOM | Wild type | $Tom_i$, $TCE_i$ |
| G4 5223 | $pTOM_{23}$ | Tn5 mutant of G4 | Tom-, TCE- |
| $PR1_{23}$ | $pTOM_{23c}$ | Phenol-utilizing revertant of G4 5223 | $Tom_c$, $TCE_c$ |
| G4 5231 | $pTOM_{31}$ | Tn5 mutant of G4 | Tom-, TCE- |
| $PR1_{31}$ | $pTOM_{31c}$ | Phenol-utilizing revertant of G4 5231 | $Tom_c$, $TCE_c$ |
| $PR1_{23}$ Cure | None | pTOM cure of $PR1_{23}$ | Tom-, TCE- |
| $PR1_{23}$ $Cure_{NR}$ | None | Spontaneous mutant of $PR1_{23}$ Cure | Tom-, TCE-, $Nal^r$, $Rif^r$ |
| *E. coli* strain | | | |
| JM109 | pRO1614 | $Tc^r$ cloning vector | Tom-, TCE- |
| JM109 | pMS64 | 11.7 kb EcoRI fragment of $pTom_{23c}$ | $Tom_c$, $TCE_c$ |

*E. coli* strains were grown and maintained on either Luria-Bertani broth (LB) or M9 minimal medium. *P. cepacia* and its derivatives were grown on either LB or Basal Salts Medium (BSM) with a single carbon source (20 mM lactate or 2 mM phenol). Antibiotic selection was carried out at 50 μg/ml kanamycin sulfate (Km), 30 μg/ml chloramphenicol (Cm), 100 μg/ml ampicillin (Ap), 25 μg/ml tetracycline (Tc), 20 μg/ml streptomycin, 100 μg/ml naladixic acid, or 50 μg/ml rifampicin (Rif) as required.

$PR1_{23}$Cure. A 2,4-dichlorophenoxyacetic acid (2,4-D) degradative plasmid (pRO101) (Kaphammer, B. J., J. J. Kukor, R. H. Olsen (1990) *J. Bacteriol.* 172:2280–2286) was conjugally transferred to $PR1_{23}$, thus enabling growth on 2,4-D. Following extended growth on 2,4-D, a spontaneous derivative was obtained that lacked $pTOM_{23}$ (Gerger, R. R., M. R. Winfrey, M. Reagin, M. S. Shields (1991) Abstr. 91st Gen. Meet. Am. Soc. Microbiol., 1991. American Society for Microbiology, Washington, D.C.).

$Rif^r$ $Nal^r$ $PR1_{23}$Cure. A $Rif^r$ colony of $PR1_{23}$ was isolated on LB Rif. This strain was likewise selected on LB Nal. The resulting $Nal^r$ strain o:$PR1_{23}Cure_{NR}$ was resistant to all Nal, Rif, and Km.

Molecular techniques. Isolation of *E. coli* and *P. cepacia* plasmids was by the Birnboim and Doly alkaline lysis technique (Birnboim, H. C., J. Doly (1979) *Nucleic Acids Res.* 7:1513–1523). Genomic DNA of *P. cepacia* was isolated by the technique of Marmur (Marmur, J. (1961) *J. Mol. Biol.* 3:208–218). Restriction endonuclease digestion, molecular cloning, Southern blot, nick translation, and autoradiography were performed according to Maniatis et al. (Maniatis, T., E. F. Ffitsch, J. Sambrook (1982) *Molecular*

Cloning: A Laboratory Manual, Cold Spring Harbor Laboratory, Cold Spring Harbor, N.Y.).

Enzyme assays and TCE analysis. Assays for catcobol 2,3-dioxygenase (C23O) activity and trifluoroheptadienoic acid (TFHA) production were performed spectrophotometrically at $A_{386}$ as previously described. TCE degradation was quantified through gas chromatographic analyses of pentane extracts as previously described (Shields, M. S., S. O. Montgomery, S. M. Cuskey, P. J. Chapman, P. H. Pritchard (1991) *Appl. Environ. Microbiol.* 57:1935–1941). Expression of Tom in JM109 (pMS64) was confirmed following growth in M9 medium containing 0.1% glucose, 0.05 mM thiamine, and one of the following: 0.5 mM toluene, phenol, o-cresol, or m-cresol. Aliquots were removed at 0, 1, 2, 3, 5, and 7 hour time intervals and analyzed via HPLC (Shields, M. S., S. O. Montgomery, P. J. Chapman, S. M. Cuskey, P. H. Pritchard (1989) *Appl. Environ. Microbiol.* 55:1624–1629).

Results

Conjugal transfer of pTOM between bacterial strains. Stability studies of pRO101 in $PR1_{23}$ ($pTOM_{23}$) revealed several isolates which had retained the ability to utilize 2,4-D, but had lost the ability to grow on phenol (Phe-). These isolates, although $Km^r$, were unable to oxidize trifluoromethylphenol (TFMP) to TFHA or to degrade TCE. Plasmid DNA preparations of Phe- isolates revealed the absence of the largest native plasmid. Constitutive Tom expression transferred by a constitutive plasmid and its expression by native pTOM promoters in *E. coli* were shown by the following conjugation: $PR1_{23}$ ($pTOM_{23c}$)× $PR1_{23}Cure_{NR}$; and $PR1_{23}$ ($pTOM_{23}$)×*E. coli* JM109 (pRO1614). Selections for the two transconjugants: $PR1_{23}Cure_{NR}$ ($pTOM_{23c}$) and JM109 (pRO1614, $pTOM_{31c}$) were carried out on BSM Phenol Rif Nal and LB Km Tc respectively. Constitutive expression of TFMP and TCE oxidation by the former had not by the latter indicated that constitutive control determinants reside on $pTOM_{23}$ (Table 11).

TABLE 11

Degradative phenotypes of parental and transconjugant strains

| Mating | Strains | Selection[1] | TFHA[2] | TCE |
|---|---|---|---|---|
| I Donor | G4 (pTOM) | Phe+, Km5 | i | i |
| Recipient | PR1₂₃ Cure | Phe-, Kmʳ | — | — |
| Transconjugant | PR1₂₃ (pTOM) | Phe+, Kmʳ | i | i |
| II Donor | PR1₂₃ (pTOM₂₃c) | Phe+ | c | c |
| Recipient | PR1₂₃ Cure_NR | Phe-, Nalʳ, Rifʳ | — | — |
| Transconjugant | PR1₂₃ Cure_NR (pTOM₂₃c) | Phe+, Nalʳ, Rifʳ | c | c |
| III Donor | PR1₃₁ | Kmʳ, Tc3 | c | c |

TABLE 11-continued

Degradative phenotypes of parental and transconjugant strains

| Mating | Strains | Selection[1] | TFHA[2] | TCE |
|---|---|---|---|---|
| Recipient | JM109 (pTOM₃₁c) (pRO1614) | Km5, Tc3 | — | — |
| Transconjugant | JM109 (pRO1614, pTOM₃₁c) | Kmʳ, Tcʳ | — | — |

[1]Selectable markers: Phe+, growth with phenol as sole carbon source; antibotic resistances as abbreviated in text.
[2]Conversion of TFMP to TFHA, or TCE oxidation was either inducible (i), constitutive (c), or undetectable (—).

Figure 5:
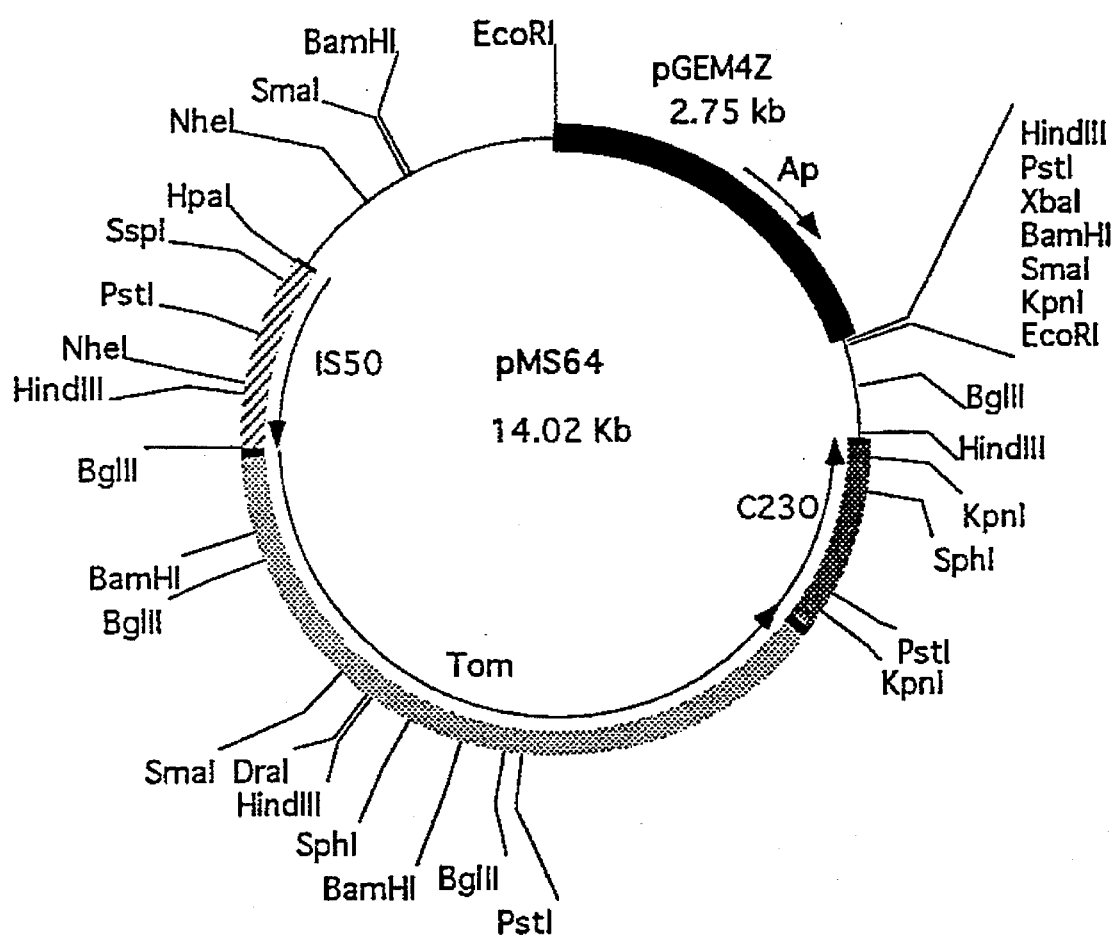
FIG. 5 shows a representation of a subclone containing an 11.2 kb EcoRI fragment of $pTOM_{23c}$, designated plasmid pMS64.

Tom and C23O activity. Following curing evidence that showed tomA and tomB located on the large plasmid, direct cloning of DNA from $pTOM_{23c}$ was carried out. $pTOM_{23c}$ was digested with EcoRI, BamHI, or HindIII and ligated to pGEM4Z. Recombinant plasmids were grown on LB Ap. One subclone containing an 11.2 kb EcoRI fragment of $pTOM_{23c}$ (designated plasmid pMS64, FIG. 5) produced a yellow product (maximal absorbance at 386 nm) when grown in the presence of phenol. *E. coli* JM109 (pMS64) containing cloned $PR1_{23c}$ DNA was shown to degrade 20 µM TCE (Table 12). HPLC analysis confirmed o-cresol production from toluene and methylcatechol from o- and m-cresol by JM109 (pMS64).

TABLE 12

TCE degradation by *E. coli* containing cloned $PR1_{23c}$ DNA

| | TCE Remaining (µM)[1] | | | |
|---|---|---|---|---|
| *E. coli* strain | LB | LB + Phenol | M9 Glucose | MP Glucose + Phenol |
| JM 109 | 16.81 | 17.73 | 14.51 | 15.24 |
| JM 109 (pMS64) | ND | 0.04 | 0.77 | 2.93 |
| Uninoculated | 16.55 | NT | NT | NT |

[1]TCE remaining in solution following an overnight incubation with cells grown as indicated. LB, Luria Broth; ND, Not Detectable; NT, Not Tested.

Hybridization. To establish the location of tomA, BamHI-digested plasmid DNA of G4 and G5 Tn5 mutants was transferred to a nitrocellulose membrane and hybridized with the nick translated 11.2 kb EcoRI fragment from pMS64 and the 2.7 kb internal BglII fragment of Tn5. The pMS64 probe hybridized with each undigested large plasmid from G4 and its derivatives. Hybridization with the internal 2.7 kb BglII Tn5 fragment revealed homology to the large plasmid of only $PR1_{23}$ but not G4 5223.

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. An isolated gene which encodes a polypeptide having an amino acid sequence selected from the group consisting of SEQ ID NO. 2, SEQ ID NO. 3, SEQ ID NO. 4, SEQ ID NO. 5, SEQ ID NO. 6, and SEQ ID NO. 7.

2. The gene, according to claim 1, wherein said gene has the nucleic acid sequence shown in SEQ ID NO. 1.

3. A microorganism which has the property of being constitutive for the degradation of hazardous chemicals selected from the group consisting of chloroaliphatic and aromatic chemicals wherein said microorganism is a host cell transformed with a gene which encodes a polypeptide having an amino acid sequence selected from the group consisting of SEQ ID NO. 2, SEQ ID NO. 3, SEQ ID NO. 4, SEQ ID NO. 5, SEQ ID NO. 6, and SEQ ID NO. 7.

* * * * *

UNITED STATES PATENT AND TRADEMARK OFFICE
CERTIFICATE OF CORRECTION

PATENT NO. : 5,543,317

DATED : August 6, 1996

INVENTOR(S) : Malcolm S. Shields and Stephen C. Francesconi

It is certified that error appears in the above-indentified patent and that said Letters Patent is hereby corrected as shown below:

Column 3: Lines 63-64: "unclescribed" should read --undescribed--.
Column 4: Line 60: "romA1." should read --tomA1.--
Column 5: Line 2: "romA4." should read --tomA4.--
Column 9: Line 39: "hornology." should read --homology.--;
Column 9: Line 54: "transgenie" should read --transgenic--
Column 11: Line 47: "metylcathechol" should read --methylcatechol--
Column 13: Line 60: "tomb" should read --tomB--
Column 14: Line 57: "tornA" should read --tomA--
Column 15: Line 48: "tomb" should read --tomB--
Column 16: Line 67: "Ffitsch" should read --Fritsch--
Column 17: Line 3: "catcobol" should read --catechol--

UNITED STATES PATENT AND TRADEMARK OFFICE
CERTIFICATE OF CORRECTION

PATENT NO. : 5,543,317

DATED : August 6, 1996

INVENTOR(S) : Malcolm S. Shields and Stephen C. Francesconi

It is certified that error appears in the above-indentified patent and that said Letters Patent is hereby corrected as shown below:

Column 17: Line 33: "($pTOM_{23}$)" should read --($pTOM_{23c}$)--
Column 17: Line 38: "had" should read --nad--
Column 18: Line 19: "HindlII" should read --HindIII--
Column 18: Line 7: "$Tc^3$" should read --$Tc^r$--
Column 18: Line 49: "BglI" should rad --BglII--

Signed and Sealed this

Twenty-ninth Day of April, 1997

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
   ( A ) LENGTH: 9785 base pairs
   ( B ) TYPE: nucleic acid
   ( C ) STRANDEDNESS: single
   ( D ) TOPOLOGY: linear ( i i ) MOLECULE TYPE: DNA (genomic)

( x i ) SEQUENCE DESCRIPTION: SEQ ID NO:1:

| | | | | | |
|---|---|---|---|---|---:|
| GGATCCTCTT | TCCCCCAGTT | CCATCCCCAA | CCCTGAGCCG | TCTATCTCGC | GCAGCGCGCT | 60 |
| CAACGACGGC | ATTCTGAGCA | TGATCCAGAC | GCCGCATGAG | TGGGTCTTCG | ACCAGAAGTA | 120 |
| CCTGGTGTAT | TGCTTCAGAT | GTCTTGTTCT | GAACGACGCC | GATGTCACTG | CATCACGGTG | 180 |
| GAAGAGGGAG | TGGCTCGATC | CGTCAGCCGA | CTACTGCCGG | GTGCACCACA | GCCTGCTCGA | 240 |
| GACTGTTCCG | CAATCGATTT | TTGCAAGAGC | TCCGAATTTC | GACGCCGCGC | TGCGGGCGAT | 300 |
| ATCACGTTAT | CGATGCCCAC | CGCTTAGGCT | GAGCAAAACA | CTACGCTAGC | AGTATTAGTG | 360 |
| AACATTGCTA | GCACTCCTTT | GGGCACGGCT | AGCATTGATT | GTGAACTCCT | ACACACGGCC | 420 |
| TGCGCAAAGT | CGTCGATCTC | ATCGGCGCTG | TACGGAAACG | GACGTCTTGC | ATGGACCGTC | 480 |
| GCGAGATCGC | TCGAAATGCC | TTTCGGCAAC | TCCTGCGCTT | CGCGCACGGC | GCGCCGCGCG | 540 |
| TGCGGACTCA | CCGACGTCGT | GAGCACCGCG | CTCACGCGCA | ATTCGGTCAC | GATGCCGATC | 600 |
| TGCCCCATAT | CAGCAATTGC | TGGGGTGTGC | ATTTCAGAAA | TTTCTGATCT | GAGCGACCTG | 660 |
| CGCCCCTTTC | CTGGTTCGCG | AATTTTATGA | CAGCGCCCCC | GCGATTTTTC | GATGTGCGAT | 720 |
| TGCCAAATGA | GCTCGACCTC | GTTTGCTAAC | ACCTCCATAG | ATACCCTGTG | TTGTATCGAT | 780 |
| TCTGTGTGAC | GGTTGTGCGT | CCTTCGGTTT | GTGCCTGGCA | GAAGGCGGCA | CCCAAACGCA | 840 |
| GGAGGCATCT | GGCCGTTTAA | CGCAGGATGC | TCGGAACGAA | TTTCGACAGA | TGACGATCTG | 900 |
| ACTCTTATAC | ACAAGTAGCG | TCCTGAACGG | AACCTTTCCC | GTTTTCCAGG | ATCTGACTTC | 960 |
| CATGTGACCT | CCTAACATGG | TAACGTTCAT | GATAACTTCT | GCTCTTCATC | GTGCGGCCGA | 1020 |
| CTGGGCTAAA | TCTGTGTTCT | CTTCGGCGGC | GCTGGGTGAT | CCTCGCCGTA | CTGCCCGCTT | 1080 |
| GGTTAACGTC | GCCGCCCAAT | TGGCAAAATA | TTCTGGTAAA | TCAATAACCA | TCTCATCAGA | 1140 |
| GGGTAGTGAA | GCCATGCAGG | AAGGCGCTTA | CCGATTTTAC | CGCAATCCCA | ACGTTTCTGC | 1200 |
| CGAGGCGATC | AGAAAGGCTG | GCGCCATGCA | AACAGTCAAG | TTGGCTCAGG | AGTTTCCCGA | 1260 |
| ACTGCTGGCC | ATTGAGGACA | CCACCTCTTT | GAGTTATCGC | CACCAGGTCG | CCGAAGAGCT | 1320 |
| TGGCAAGCTG | GGCTCTATTC | AGGATAAATC | CCGCGGATGG | TGGGTTCACT | CCGTTCTCTT | 1380 |
| GCTCGAGGCC | ACCACATTCC | GCACCGTAGG | ATTACTGCAT | CAGGAGTGGT | GGATGCGCCC | 1440 |
| GGATGACCCT | GCCGATGCGG | ATGAAAAGGA | GAGTGGCAAA | TGGCTGGCAG | CGGCCGCAAC | 1500 |
| TAGCCGGTTA | CGCATGGGCA | GCATGATGAG | CAACGTGATT | GCGGTCTGTG | ACCGCGAAGC | 1560 |
| CGATATTCAT | GCTTATCTGC | AGGACAGGCT | GGCGCATAAC | GAGCGCTTCG | TGGTGCGCTC | 1620 |
| CAAGCACCCA | CGCAAGGACG | TAGAGTCTGG | GTTGTATCTG | ATCGACCATC | TGAAGAACCA | 1680 |
| ACCGGAGTTG | GGTGGCTATC | AGATCAGCAT | TCCGCAAAAG | GCGTGGTGG | ATAAACGCGG | 1740 |
| TAAACGTAAA | AATCGACCAG | CCCGCAAGGC | GAGCTTGAGC | CTGCGCAGTG | GGCGCATCAC | 1800 |
| GCTAAACAG | GGGAATATCA | CGCTCAACGC | GGTGCTGGCC | GAGGAGATTA | CCCGCCCAA | 1860 |
| GGGTGAGACC | CCGTTGAAAT | GGTTGTTGCT | GACCGGCGAA | CCGGTCGAGT | CGCTAGCCCA | 1920 |
| AGCCTTGCGC | GTCATCGACA | TTTATACCCA | TCGCTGGCGG | ATCGAGGAGT | TCCATAAGGC | 1980 |
| ATGGAAAACC | GGAGCAGGAG | CCGAGAGGCA | ACGCATGGAG | GAGCCGGATA | ATCTGGAGCG | 2040 |
| GATGGTCTCG | ATCCTCTCGT | TTGTTGCGGT | CAGGCTGTTA | CAGCTCAGAG | AAAGCTTCAC | 2100 |

```
GCTGCCGCAA GCACTCAGGG CGCAAGGGCT GCTAAAGGAA GCGGAACACG TAGAAAGCCA      2160
GTCCGCAGAA ACGGTGCTGA CCCCGGATGA ATGTCAGCTA CTGGGCTATC TGGACAAGGG      2220
AAAACGCAAG CGCAAAGAGA AAGCAGGTAG CTTGCAGTGG GCTTACATGG CGATAGCTAG      2280
ACTGGGCGGT TTTATGGACA GCAAGCGAAC CGGAATTGCC AGCTGGGGCG CCCTCTGGTA      2340
AGGTTGGGAA GCCCTGCAAA GTAAACTGGA TGGCTTTCTT GCCGCCAAGG ATCTGATGGC      2400
GCAGGGGATC AAGATCTGAT CAAGAGACAG CCGCAGCAGC TCAACTGTAA ATTCGTTGCT      2460
GCAAAGCAGC AATAATGGCA CGTTGCTACC GATGGCACGG GGCTTGCTTC GGAATATGAA      2520
AACACAGAAT CGTGAAAACA CGGAATCGGA GACACAGGCG ATGCACAAGC AAGCAGCCCT      2580
TGAGGCGGAA CCCAGGTTCG ATCCGAACCT CAGGTTTGTC ACGTTACCGC CATCAACACA      2640
CAGGGATTCG TCCAGTTCGA ATTTTCAGTT GGCACCCCCG AGCTCTGTGT CGAGCTCATG      2700
CTGCCCGTTG CTGCGTTCGA AGAATTTTGC CTCGCGCAGA AGGTGACGCG ATTGGATGCC      2760
TTCGGCGAGA TTGTGCGGCA TTGATTTTCT TGTGAGCAGC GCCGAGCAGC CTGATGAAGC      2820
GCGCCTAGTC TGATCGCATC CCATCCCGGT TCACAACCAC AGGAGCAGTT AATGACCATC      2880
GATTTGAAGA CGCGGGAAAT CAAACCACTG CGTCACACCT ACACGCACGT GGCTCAATAC      2940
ATCGGAGCCG ATAAAGCCGC TTCGCGCTAT CAGGAAGGCA CTGTAGGTGC TCAACCCGCA      3000
GCGAATTTTC ATTACCGGCC CACGTGGGAT CCCGAGCATG AACTGTTCGA CACGTCGCGT      3060
ACCGCGATTC AAATGAAGGA CTGGTATGCG CTGAAAGACC CGCGTCAGTT CTACTACGCG      3120
TCGTGGACGA TGACCCGAGC GCGGCAGCAA GACGCGATGG AATCCAACTT CGAGTTTGTC      3180
GAGTCGCGCG GCATGATCGA TCTCGTTTCC GATGAGGTTC GACAACGGGC GCTTTCCGTT      3240
CTCGTGCCTT TGCGTCACGC GGCCTGGGGC GCGAACATGA ACAACTCCCA GATCTGTGCC      3300
CTAGGTTATG GCACGACCTT CACTGCGCCG GCTATGTTCC ACGCAATGGA CAATCTGGGT      3360
GTAGCGCAGT ATCTCACACG ACTGGCGCTG GTAATGTCTG GACCCGATCT TCTTGACGAA      3420
GCCAAGCAAG CCTGGATGAC GAGTCCCGAT TGGCAACCGT TGCGTCGTTA TGTGGAAAAC      3480
ACTCTGGTGC TGCAAGATCC GGTGGAACTG TTCATCGCCC AAAATCTGGC GCTCGACGGT      3540
CTTCTTTATC CCATGATCTA CGGCGCTTTC GTCGACGATT ACATCGCACT CAACGGTGGT      3600
AGCGCAGTGG CAATGCTAAC CACTTTCATG CCCGAGTGGC ATGACGAATC CAGTCGCTGG      3660
GTCGATGCGG TAGTAAAGAC CATGGCGACG GAATCGGAGG ATAACAAAGC GCTGCTCATT      3720
CACTGGTTGC GTACCTGGGA AGATCAGGCG GCGTCAGCGT TGTTGCCTGT CGCTGAAATG      3780
GCTTTGGCGG AAAACGGCCA CGACGCCTTG GAAGAAGTAA GGCAGCAACT TCGTGCCGCG      3840
TTGCGAAGGC CGGGATTGTT CTGTAACCCC TAATTTATAT TCCTGACCGT CATAGAGGAA      3900
TGTTCATGTC TAACGTATTT ATCGCGTTTC AGGCTAACGA GGAGTCTCGA CCGGTGGTGG      3960
AGGCGATTCT CGCTGATAAC CCTAAGGCGG TCGCCACAGA ATCGCCTGGC ATGGTGAAGA      4020
TCGATGCGCC CGGGCATCTC ACAATAAACC GTCAAAGCAT CGAAGACCGG ATCGGCATGA      4080
AGTTCGATCT CCAGCAAATC CACATCAACC TGATCACCTT GTCCGGATAT ATCGACGAGG      4140
ATGACGAACA GTTCACGCTG AGCTGGAAAC ACTGAACACG GCAAAGAGGA AATTGAAATG      4200
GACACTTCTG TGCAGAAGAA GAAACTCGGT TTAAAGGATC GCTACGCAGC GATGACCCGC      4260
GGTCTTGGCT GGCAGACCAG CTACCAGCCG ATGGAGAAAG TGTTTCCGTA CGACAAGTAC      4320
GAAGGCATCA AGATCCACGA TTGGGATAAA TGGAAGACC CCTTCCGCCT GACCATGGAC      4380
GCCTACTGGA AATATCAGGG CGAGAAGGAA AAAAAGCTTT ACGCCGTCAT CGACGCTTTC      4440
GCGCAGAACA ACGGGCAGTT GAGCATTTCC GACGCGCGAT ATGTCAACGC ACTCAAGGTG      4500
```

```
TTTATCCAGG GTGTGACACC GTTGGAGTAT ATGGCACACC GAGGTTTTGC CCACATTGGT    4560
CGGCATTTTA CGGGTGAAGG GGCACGTGTT GCTTGCCAGA TGCAGTCCAT CGACGAGCTG    4620
CGTCACTTCC AGACCGAAAT GCATGCTCTC TCGCACTACA ACAAGTATTT TAACGGTCTG    4680
CACAACTCCA TCCATTGGTA CGACCGGGTT TGGTATTTGT CGGTGCCCAA GTCATTTTTT    4740
GAAGACGCGG CCACCGGTGG ACCGTTCGAG TTTCTTACCG CGGTGAGCTT TCGTTCGAA     4800
TATGTGTTGA CCAACCTGCT GTTTGTCCCC TTCATGTCGG GTGCTGCTTA CAACGGGGAC    4860
ATGTCTACGG TCACTTTCGG TTTTTCGGCG CAAAGTGACG AATCGCGCCA CATGACACTC    4920
GGCATCGAAT GCATCAAGTT CATGCTGGAA CAGGATCCGG ACAACGTGCC CATCGTGCAG    4980
CGCTGGATCG ACAAGTGGTT CTGGCGCGGC TATCGGCTGT TGAGCATCGT GGCCATGATG    5040
CAGGACTACA TGCTGCCCAA CCGGGTGATG AGCTGGCGCG AGAGCTGGGA GATGTACGTC    5100
GAGCAGAACG GCGGCCGCTG TTCAAGGATC TTCCTTATGG CATCCGCAAG CCCAAGGGCT    5160
GGGACCAGGC TTGCGAAGGC AAGGACCACA TCAGCCATCA GACCTTCGCG GTATTCTATA    5220
ACTATAACGC CGCGGCCCCC ATCCACACCT GGGTTCCCAC AAAAGAAGAA ATGGGATGGC    5280
TGTCGGAGAA GTACCCCGAG ACGTTCGACA AGTATTACCG TCCGCGTTGG GACTACTGGC    5340
GCGAGCAGGC CGCCAAGGGC AACCGTTTCT ACAACAAGAC GCTGCCGATG CTCTGCACTA    5400
CCTGCCAGAT TCCGATGATA TTCACCGAGC CTGGCGACGC AACCAAGATC TGCTATCGCG    5460
AGTCGGCCTA CCTCGGCGAC AAGTATCACT TCTGCAGCGA CCACTGCAAG GAGATTTTTG    5520
ACAACGAACC CGAAAAGTTC GTGCAGTCAT GGCTTCCGCC GCAGCAAGTG TATCAAGGAA    5580
ACTGTTTCAA GCCGGATGCC GATCCGACCA AGGAGGGTTT TGATCCCTTG ATGGCCTTGC    5640
TCGACTACTA CAACCTGAAT GTAGGCCGGG ACAACTTCGA TTTCGAGGGA TCGGAAGACC    5700
AAAAGAACTT TGCTGCCTGG CGTGGAGAGG TCTTGCAAGG AGAAGCCAAA TGAGCGTTGT    5760
TGCCCTCAAA CCCTACAAGT TCCCGGCACG AGACGCGCGC GAAAACTTTC CGGCGCCGTT    5820
GCTGTTTATC GGCTGGGAAG ACCATCTGTT GTTTGCGGCA CCTGTTGCCT TGCCCCTGCC    5880
GTCGGACACG TTGTTCGGTG CGCTGTGCAC CCAGGTGTTG CCCGGCACTT ATGGCTATCA    5940
CCCCGATTTC TCAAAGATCG ACTGGAGCCA GGTGCAGTGG TTTAAGTCCG CCAGCCGTG    6000
GCATCCCGAC CCGGCGAAGT CGCTGGCTGA AAACGGTCTG ACGCACAAAG ACGTGATCCG    6060
CTTTCGCACG CCTGGCTTGA ACGGTCTGAG CGGTTCCTGC AATTGAGATT GCGTCATGGC    6120
AGCGCAATCA CACCGCAGCC GAAGTTACAG GCCGCGGTGT GATTGGCCTC CGGCGATTTG    6180
AACAATGACC TATCAACTCA ACATTCAGCC CCTGGGCGCA CCATTGAGGT GGAGGAAGGG    6240
CAAACTATAC TCGACGCGGC CTTGCGCCAA GGCATTTACA TTCCGCACGC GTGTGGTCAC    6300
GGGCTATGTG GAACCTGCAA GGTGCAGGTG TGTGACGGAG AAGTCGATCT CGGCGATGCG    6360
AATCCCTTCG CGCTGATGGA CTTCGAGCGC GAGGACCAAG GCTTGGCCT GCTGCGCCAC    6420
CTTGCTCGAT GACACGACCA TCGAGGCCGA CATCGAGGAA GACCCGGACG CCGAAGTCAT    6480
CCCGGTCGAG GATTTCAATG CCGAGGTGAC ACGCATCGAG CAACTCACAC CGACGATCAA    6540
AGCCGTCTTC CTGAGACTCG ATCAACCGAT TCATTTTCAG GCGGGTCAGT ACGTGCAACT    6600
TGAAATTCCC GAGTTGCGCC AGACACGGGC GTTTTCCATC GCCAATTCAC CTGCGGACGT    6660
CGCAGCAACG GGAGAGATCG AGCTCAATAT TCGCCGGGTT CCGGGAGGAC AGGGCACGGG    6720
TTACATCCAT GAACAACTGG CGGTGGGGAA CATTCTGCAC GTGACGGGTC CCTATGGCCG    6780
GTTTTTCGTG CGCAGGTCAG CCGACCAGCC CATGGTTTTC ATGGCAGGTG GTTCAGGCCT    6840
GTCGAGCCCT CGGTCGATGA TTCTCGACTT GTTGCAAAGC GGATGGAGCA AGCCTATCAC    6900
```

```
CCTGATCTAT  GGCCAGCGCA  ATGAGGCAGA  ACTGTATTAC  GACGAGGAGT  TCGCGAGCTC  6960
GGCCAGCGGT  ATTCGAACTT  CAGCTACGTA  CCGGCACTAT  CGGAAAAAGC  AGAAGGTGCG  7020
ACGCATCCCT  TGGCGCAGGG  TTTCGTTCAC  GAGGTCGCCA  AAGCTCATTT  CGAGAACAAC  7080
TTTTCCGGCC  ACAAAGCCTA  TTTGTGCGGG  CCGCCGGCAA  TGATCGACGC  CTGCGTCACG  7140
ACCCTGATCC  AGGGCCGGTT  GTTCGAACGC  GACATCTATT  TTGAGAAGTT  CATTTCCGCA  7200
GCCGATGCCC  AACAAGTACG  CAGTCCGCTT  TTCAAGAGGG  TGTGATCGTG  ACTACTCAGG  7260
ACGGGAAGGT  CTACGTGACC  GTCAAGCAGA  CCGGCGACGT  TTCAGCTGCG  CTCTGGGTGA  7320
GTCTCTGCTT  TCCGGCATGG  CACCTTGGGC  GTCGCGGCAT  ACCAGTTGGT  TGCCTTAGCG  7380
GCGGGTGCGG  AGTGTGTAAG  GTCGCGGTGT  GCAGAGGCAG  CGTGCGCAAA  ACTGGAGCAA  7440
TGAGCCGTGC  GCACATTTCC  GAGGCGGAAG  AAGCGCAAGG  TGTGGTGCTG  GCGTGCCGGG  7500
TGGCTCCCAC  TGATGATGTG  GAACTGGAGG  TGGTCGGCAA  GATGCAAAAG  CCCTTTTTCA  7560
AAGGGTTCAG  CTTTCAGGTA  GCCCAAGATT  CAACGAAATA  AGCCGAAGGA  GATTAGACCA  7620
TGAGTGTGAT  GCGAATCGGC  CATGCGAGTC  TGAAAGTGAT  GGACATGGCG  TTGGCAATCA  7680
AGCACTACGA  AAACGTCCTG  GAATGAAAAG  GACGATGGAG  GACGAACATG  GAAATGTGTA  7740
CCTCAAATGC  TGGGACGAAT  GGGACAAGTA  CTCGGTGATT  CTGACGCCGT  CCGATCAAGC  7800
GGGGCTCAAC  CATGTCGCCT  ACAAGGTTGA  GCACGATGCC  GACCTGAATG  CGCTGCAAAA  7860
GCGTATCGAA  GCCTATGGCA  TCAAGACACA  AATGCTCCCC  GAAGGTACCG  CCAGACACGC  7920
CAATACCCCC  GATGCGATGG  CCACTTTCAA  CAATCGGCAA  ACCACCGCCG  AAGGCGATGA  7980
AGCGGGGCCT  TCGCACGATG  CCTTGGCGGA  CCGCTTCGGA  ATGACTCAGC  AAGGCCTCAC  8040
TCCACCGACT  GGTCGTAAGC  CGAAACTGGC  TGCCGTGTAT  GCCTTGTCGA  TGGCGATCTC  8100
GATGGAGTGC  AACGCGCTCC  AGGCATGCGC  AGAAACGCGG  CAAGATTCCC  CGCCACGTCG  8160
ACCACCGCGA  TGTTCACGCA  TACGCCGAGG  CCTGCGGCTG  CATCGCAGCT  GCCTCGACGA  8220
CGCGGTTAGC  CGCAGGCCAG  TTGATCAGCC  GCGCCTCGAC  GCTATGAAGT  GAGTCAGCCT  8280
GAGTCATGTG  CTATCTCCTG  CGTGGCAGTC  AGGTGTAAAC  CTCGGTGAAC  GACTGGACCA  8340
ACTCCCCGGT  GTGATAGAAG  ATGCCGCTGC  CGAGATGCTC  TTCCGTCCAG  GTCGTCACAG  8400
GCCGATCAGG  TTGAGCGAGG  TAGCCCAGGC  CGGCAAAGGT  CTCGTTGCGA  TTCCCACAAG  8460
GATCGAAGAA  ATAGATTGTC  TCCCGCGGGT  AATCCCATGG  CGAGTCGGCG  CCACGTCGAT  8520
CTTGACTTGT  TCTTGGCCAT  GACGTCGGCC  GATTTCAGTA  CGTCATGCCA  CGAGTCGAGG  8580
AAGAAGGCAA  TGTGGTGCAA  GCCATTGCGA  GGCCCACCTA  CGAAAGCGAT  GTCGTGCGGC  8640
GTGGACGTGC  GGAACATCCA  CGTTGCAGCC  TGAATGCTAC  TATCCGGACC  TACCATAACT  8700
TGCTCAGCCA  GATAAAAGTC  CAGGCATTCC  TTCATGAATC  GGGTATTTTC  CGCCACCCGA  8760
TTCACGCCGT  CTCCGGATTG  AGTTCACACA  TCAATAGGCA  GTGATCCAGC  CAATGCGCCT  8820
GCCCCCTTGA  CGTCATCGGG  CCACGGGTCA  GGATTGGTCG  TTCCGACTCC  GGTGCCCACA  8880
TATTCCTTCG  TCGCAAACAG  ACGCATCTCA  TGTCCGCTCG  GCAGGTTGAA  CTGCAGCATA  8940
CGACCGGTCG  AAGGAAGGGT  ACCGAAGAGC  AGGACGAGCA  CTGTGCGCAA  GCCGGATTGA  9000
GCCTGCTAGG  TCTAACTCAA  ACCTGAATCT  TTCCGGAAAG  TCGACTGCCG  CCGCGACCAC  9060
ATTTGCCTAA  TAGGAAGCTT  ACTAAAACAT  CATGCTGATT  ACCGATCCCC  AAGCGACCGC  9120
GAGCACTGGA  AACCAGTCCG  ACGCTCATGC  TAAAGAATCC  ACAACTTCAT  CAACGGCGAA  9180
TATGTGCCGG  GTCAGCGTTG  GTTCGAGAAG  CGCTCGCCGT  TGAATAACGC  GGTCATTGCC  9240
AAGGTGGCCG  AAGCCGGCCG  TGCCGAAGTC  GACGCGGCGG  TGGCTGCGGC  CAGGCGCTTA  9300
```

```
AGGGAGCGTG GGGGCGCATG AGCTTGGCCC AGCGCGTGGA AGTGCTGTAC GCGGTGGCCG      9360

ACGGCATCAA CCGTCGTTTT GACGACTTCC TTGCCGCTGA GGTAGAGGAC ACGGGCAAGC      9420

CTATGAGCCT AGCGCGGCAT GTGGACATTC CGCGTGGGGC GGCCAATTTC AAGATCTTTG      9480

CCGACGTGGT GAAGAACGTA CCCACTGAGT TTTTTGAAAT GCCTACACCG GATGGGGGCG      9540

ATCAACTACG CCATGCGTCG ACCGGTGGGG GTGGTCGGGG TGATCTGTCC ATGGAACCTG      9600

CGCTGCTGCT GATGACCTGG AAAGTCGGCC CAGCGCTGGC CTGTGGCAAC ACCGTTGTGG      9660

TCAAGCCCTC CGAAGAGACG CCGCAGACCG CTGCATTGCT GGGCGAAGTG ATGAACACGG      9720

CGGGCGTGCC GCCAGGGGTC TACAACGTCG TGCACGGCTT CGGCCCCAAC TCCACCGGCG      9780

AATTC                                                                  9785
```

( 2 ) INFORMATION FOR SEQ ID NO:2:

( i ) SEQUENCE CHARACTERISTICS:
    ( A ) LENGTH: 331 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:2:

```
Met Thr Ile Asp Leu Lys Thr Arg Glu Ile Lys Pro Leu Arg His Thr
  1               5                  10                  15

Tyr Thr His Val Ala Gln Tyr Ile Gly Ala Asp Lys Ala Ala Ser Arg
                 20                  25                  30

Tyr Gln Glu Gly Thr Val Gly Ala Gln Pro Ala Ala Asn Phe His Tyr
             35                  40                  45

Arg Pro Thr Trp Asp Pro Glu His Glu Leu Phe Asp Thr Ser Arg Thr
 50                  55                  60

Ala Ile Gln Met Lys Asp Trp Tyr Ala Leu Lys Asp Pro Arg Gln Phe
 65                  70                  75                  80

Tyr Tyr Ala Ser Trp Thr Met Thr Arg Ala Arg Gln Gln Asp Ala Met
                 85                  90                  95

Glu Ser Asn Phe Glu Phe Val Glu Ser Arg Gly Met Ile Asp Leu Val
            100                 105                 110

Ser Asp Glu Val Arg Gln Arg Ala Leu Ser Val Leu Val Pro Leu Arg
            115                 120                 125

His Ala Ala Trp Gly Ala Asn Met Asn Asn Ser Gln Ile Cys Ala Leu
    130                 135                 140

Gly Tyr Gly Thr Thr Phe Thr Ala Pro Ala Met Phe His Ala Met Asp
145                 150                 155                 160

Asn Leu Gly Val Ala Gln Tyr Leu Thr Arg Leu Ala Leu Val Met Ser
                165                 170                 175

Gly Pro Asp Leu Leu Asp Glu Ala Lys Gln Ala Trp Met Thr Ser Pro
            180                 185                 190

Asp Trp Gln Pro Leu Arg Arg Tyr Val Glu Asn Thr Leu Val Leu Gln
            195                 200                 205

Asp Pro Val Glu Leu Phe Ile Ala Gln Asn Leu Ala Leu Asp Gly Leu
    210                 215                 220

Leu Tyr Pro Met Ile Tyr Gly Ala Phe Val Asp Asp Tyr Ile Ala Leu
225                 230                 235                 240

Asn Gly Gly Ser Ala Val Ala Met Leu Thr Thr Phe Met Pro Glu Trp
                245                 250                 255
```

```
        His  Asp  Glu  Ser  Ser  Arg  Trp  Val  Asp  Ala  Val  Val  Lys  Thr  Met  Ala
                       260                      265                      270

Thr  Glu  Ser  Glu  Asp  Asn  Lys  Ala  Leu  Leu  Ile  His  Trp  Leu  Arg  Thr
                       275                      280                      285

Trp  Glu  Asp  Gln  Ala  Ala  Ser  Ala  Leu  Leu  Pro  Val  Ala  Glu  Met  Ala
                       290                      295                      300

Leu  Ala  Glu  Asn  Gly  His  Asp  Ala  Leu  Glu  Glu  Val  Arg  Gln  Gln  Leu
        305                      310                      315                      320

Arg  Ala  Ala  Leu  Arg  Arg  Pro  Gly  Leu  Phe  Cys
                            325                      330
```

( 2 ) INFORMATION FOR SEQ ID NO:3:

( i ) SEQUENCE CHARACTERISTICS:
        ( A ) LENGTH: 92 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

```
        Met  Phe  Met  Ser  Asn  Val  Phe  Ile  Ala  Phe  Gln  Ala  Asn  Glu  Glu  Ser
        1                    5                       10                       15

Arg  Pro  Val  Val  Glu  Ala  Ile  Leu  Ala  Asp  Asn  Pro  Lys  Ala  Val  Ala
                       20                      25                       30

Thr  Glu  Ser  Pro  Gly  Met  Val  Lys  Ile  Asp  Ala  Pro  Gly  His  Leu  Thr
                       35                      40                       45

Ile  Asn  Arg  Gln  Ser  Ile  Glu  Asp  Arg  Ile  Gly  Met  Lys  Phe  Asp  Leu
        50                       55                       60

Gln  Gln  Ile  His  Ile  Asn  Leu  Ile  Thr  Leu  Ser  Gly  Tyr  Ile  Asp  Glu
        65                       70                       75                       80

Asp  Asp  Glu  Gln  Phe  Thr  Leu  Ser  Trp  Lys  His  Glx
                            85                       90
```

( 2 ) INFORMATION FOR SEQ ID NO:4:

( i ) SEQUENCE CHARACTERISTICS:
        ( A ) LENGTH: 519 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

```
        Met  Asp  Thr  Ser  Val  Gln  Lys  Lys  Leu  Gly  Leu  Lys  Asp  Arg  Tyr
        1                    5                       10                       15

Ala  Ala  Met  Thr  Arg  Gly  Leu  Gly  Trp  Gln  Thr  Ser  Tyr  Gln  Pro  Met
                       20                      25                       30

Glu  Lys  Val  Phe  Pro  Tyr  Asp  Lys  Tyr  Glu  Gly  Ile  Lys  Ile  His  Asp
                       35                      40                       45

Trp  Asp  Lys  Trp  Glu  Asp  Pro  Phe  Arg  Leu  Thr  Met  Asp  Ala  Tyr  Trp
                50                       55                       60

Lys  Tyr  Gln  Gly  Glu  Lys  Glu  Lys  Leu  Tyr  Ala  Val  Ile  Asp  Ala
        65                       70                       75                       80

Phe  Ala  Gln  Asn  Asn  Gly  Gln  Leu  Ser  Ile  Ser  Asp  Ala  Arg  Tyr  Val
                            85                       90                       95

Asn  Ala  Leu  Lys  Val  Phe  Ile  Gln  Gly  Val  Thr  Pro  Leu  Glu  Tyr  Met
                       100                      105                      110
```

| | | | | | | | | | | | | | | |
|---|---|---|---|---|---|---|---|---|---|---|---|---|---|---|
| Ala | His | Arg 115 | Gly | Phe | Ala | His | Ile 120 | Gly | Arg | His | Phe | Thr 125 | Gly | Glu | Gly |
| Ala | Arg 130 | Val | Ala | Cys | Gln | Met 135 | Gln | Ser | Ile | Asp | Glu 140 | Leu | Arg | His | Phe |
| Gln 145 | Thr | Glu | Met | His | Ala 150 | Leu | Ser | His | Tyr | Asn 155 | Lys | Tyr | Phe | Asn | Gly 160 |
| Leu | His | Asn | Ser | Ile 165 | His | Trp | Tyr | Asp | Arg 170 | Val | Trp | Tyr | Leu | Ser 175 | Val |
| Pro | Lys | Ser | Phe 180 | Phe | Glu | Asp | Ala | Ala 185 | Thr | Gly | Gly | Pro | Phe 190 | Glu | Phe |
| Leu | Thr | Ala 195 | Val | Ser | Phe | Ser | Phe 200 | Glu | Tyr | Val | Leu | Thr 205 | Asn | Leu | Leu |
| Phe | Val 210 | Pro | Phe | Met | Ser | Gly 215 | Ala | Ala | Tyr | Asn | Gly 220 | Asp | Met | Ser | Thr |
| Val 225 | Thr | Phe | Gly | Phe | Ser 230 | Ala | Gln | Ser | Asp | Glu 235 | Ser | Arg | His | Met | Thr 240 |
| Leu | Gly | Ile | Glu | Cys 245 | Ile | Lys | Phe | Met | Leu 250 | Glu | Gln | Asp | Pro | Asp 255 | Asn |
| Val | Pro | Ile | Val 260 | Gln | Arg | Trp | Ile | Asp 265 | Lys | Trp | Phe | Trp | Arg 270 | Gly | Tyr |
| Arg | Leu | Leu 275 | Ser | Ile | Val | Ala | Met 280 | Met | Gln | Asp | Tyr | Met 285 | Leu | Pro | Asn |
| Arg | Val 290 | Met | Ser | Trp | Arg | Glu 295 | Ser | Trp | Glu | Met | Tyr 300 | Val | Glu | Gln | Asn |
| Gly 305 | Gly | Ala | Leu | Phe | Lys 310 | Asp | Leu | Ala | Arg | Tyr 315 | Gly | Ile | Arg | Lys | Pro 320 |
| Lys | Gly | Trp | Asp | Gln 325 | Ala | Cys | Glu | Gly | Lys 330 | Asp | His | Ile | Ser | His 335 | Gln |
| Thr | Phe | Ala | Val 340 | Phe | Tyr | Asn | Tyr | Asn 345 | Ala | Ala | Ala | Pro | Ile 350 | His | Thr |
| Trp | Val | Pro 355 | Thr | Lys | Glu | Glu | Met 360 | Gly | Trp | Leu | Ser | Glu 365 | Lys | Tyr | Pro |
| Glu | Thr 370 | Phe | Asp | Lys | Tyr | Tyr 375 | Arg | Pro | Arg | Trp | Asp 380 | Tyr | Trp | Arg | Glu |
| Gln 385 | Ala | Ala | Lys | Gly | Asn 390 | Arg | Phe | Tyr | Asn | Lys 395 | Thr | Leu | Pro | Met | Leu 400 |
| Cys | Thr | Thr | Cys | Gln 405 | Ile | Pro | Met | Ile | Phe 410 | Thr | Glu | Pro | Gly | Asp 415 | Ala |
| Thr | Lys | Ile | Cys 420 | Tyr | Arg | Glu | Ser | Ala 425 | Tyr | Leu | Gly | Asp | Lys 430 | Tyr | His |
| Phe | Cys | Ser 435 | Asp | His | Cys | Lys | Glu 440 | Ile | Phe | Asp | Asn | Glu 445 | Pro | Glu | Lys |
| Phe | Val 450 | Gln | Ser | Trp | Leu | Pro 455 | Pro | Gln | Gln | Val | Tyr 460 | Gln | Gly | Asn | Cys |
| Phe 465 | Lys | Pro | Asp | Ala | Asp 470 | Pro | Thr | Lys | Glu | Gly 475 | Phe | Asp | Pro | Leu | Met 480 |
| Ala | Leu | Leu | Asp | Tyr 485 | Tyr | Asn | Leu | Asn | Val 490 | Gly | Arg | Asp | Asn | Phe 495 | Asp |
| Phe | Glu | Gly | Ser 500 | Glu | Asp | Gln | Lys | Asn 505 | Phe | Ala | Ala | Trp | Arg 510 | Gly | Glu |
| Val | Leu | Gln 515 | Gly | Glu | Ala | Lys | | | | | | | | | |

( 2 ) INFORMATION FOR SEQ ID NO:5:

( i ) SEQUENCE CHARACTERISTICS:
    ( A ) LENGTH: 93 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:5:

| Met | Ser | Val | Val | Ala | Leu | Lys | Pro | Tyr | Lys | Phe | Pro | Ala | Arg | Asp | Ala |
|---|---|---|---|---|---|---|---|---|---|---|---|---|---|---|---|
| 1 | | | | 5 | | | | | 10 | | | | | 15 | |
| Arg | Glu | Asn | Phe | Pro | Ala | Pro | Leu | Leu | Phe | Ile | Gly | Trp | Glu | Asp | His |
| | | | 20 | | | | 25 | | | | | 30 | | | |
| Leu | Leu | Phe | Ala | Ala | Pro | Val | Ala | Leu | Pro | Leu | Pro | Ser | Asp | Thr | Leu |
| | | 35 | | | | 40 | | | | | 45 | | | | |
| Phe | Gly | Ala | Leu | Cys | Thr | Gln | Val | Leu | Pro | Gly | Thr | Tyr | Gly | Tyr | His |
| | 50 | | | | | 55 | | | | | 60 | | | | |
| Pro | Asp | Phe | Ser | Lys | Ile | Asp | Trp | Ser | Gln | Val | Gln | Trp | Phe | Lys | Ser |
| 65 | | | | | 70 | | | | 75 | | | | | | 80 |
| Gly | Gln | Pro | Trp | His | Pro | Asp | Pro | Ala | Lys | Ser | Leu | Ala | | | |
| | | | | 85 | | | | | 90 | | | | | | |

( 2 ) INFORMATION FOR SEQ ID NO:6:

( i ) SEQUENCE CHARACTERISTICS:
    ( A ) LENGTH: 351 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:6:

| Met | Thr | Tyr | Gln | Leu | Asn | Ile | Gln | Pro | Leu | Gly | Ala | Pro | Glu | Val | Glu |
|---|---|---|---|---|---|---|---|---|---|---|---|---|---|---|---|
| 1 | | | | 5 | | | | | 10 | | | | | 15 | |
| Glu | Gly | Gln | Thr | Ile | Leu | Asp | Ala | Ala | Leu | Arg | Gln | Gly | Ile | Tyr | Ile |
| | | | 20 | | | | | 25 | | | | | 30 | | |
| Pro | His | Ala | Cys | Gly | His | Gly | Leu | Cys | Gly | Thr | Cys | Lys | Val | Gln | Val |
| | | 35 | | | | | 40 | | | | | 45 | | | |
| Cys | Asp | Gly | Glu | Val | Asp | Leu | Gly | Asp | Ala | Asn | Pro | Phe | Ala | Leu | Met |
| | 50 | | | | | 55 | | | | | 60 | | | | |
| Asp | Phe | Glu | Arg | Glu | Asp | Lys | Gly | Leu | Ala | Cys | Cys | Ala | Thr | Leu | Leu |
| 65 | | | | | 70 | | | | | 75 | | | | | 80 |
| Asp | Asp | Thr | Thr | Ile | Glu | Ala | Asp | Ile | Glu | Glu | Asp | Pro | Asp | Ala | Glu |
| | | | | 85 | | | | | 90 | | | | | 95 | |
| Val | Ile | Pro | Val | Glu | Asp | Phe | Asn | Ala | Glu | Val | Thr | Arg | Ile | Glu | Gln |
| | | | 100 | | | | | 105 | | | | | 110 | | |
| Leu | Thr | Pro | Thr | Ile | Lys | Ala | Val | Phe | Leu | Arg | Leu | Asp | Gln | Pro | Ile |
| | | | 115 | | | | | 120 | | | | | 125 | | |
| His | Phe | Gln | Ala | Gly | Gln | Tyr | Val | Gln | Leu | Glu | Ile | Pro | Glu | Leu | Arg |
| | | | 130 | | | | | 135 | | | | | 140 | | |
| Gln | Thr | Arg | Ala | Phe | Ser | Ile | Ala | Asn | Ser | Pro | Ala | Asp | Val | Ala | Ala |
| 145 | | | | | 150 | | | | | 155 | | | | | 160 |
| Thr | Gly | Glu | Ile | Glu | Leu | Asn | Ile | Arg | Arg | Val | Pro | Gly | Gly | Gln | Gly |
| | | | | 165 | | | | | 170 | | | | | 175 | |
| Thr | Gly | Tyr | Ile | His | Glu | Gln | Leu | Ala | Val | Gly | Asn | Ile | Leu | His | Val |
| | | | 180 | | | | | 185 | | | | | 190 | | |
| Thr | Gly | Pro | Tyr | Gly | Arg | Phe | Phe | Val | Arg | Arg | Ser | Ala | Asp | Gln | Pro |
| | | | 195 | | | | | 200 | | | | | 205 | | |

```
Met  Val  Phe  Met  Ala  Gly  Gly  Ser  Gly  Leu  Ser  Ser  Pro  Arg  Ser  Met
     210                      215                 220

Ile  Leu  Asp  Leu  Leu  Gln  Ser  Gly  Trp  Ser  Lys  Pro  Ile  Thr  Leu  Ile
225                      230                 235                           240

Tyr  Gly  Gln  Arg  Asn  Glu  Ala  Glu  Leu  Tyr  Tyr  Asp  Glu  Glu  Phe  Glu
                245                      250                           255

Leu  Gly  Gln  Arg  Tyr  Ser  Asn  Phe  Ser  Tyr  Val  Pro  Ala  Leu  Ser  Glu
               260                      265                      270

Lys  Ala  Glu  Gly  Ala  Thr  His  Pro  Leu  Ala  Gln  Gly  Phe  Val  His  Glu
          275                      280                 285

Val  Ala  Lys  Ala  His  Phe  Glu  Asn  Asn  Phe  Ser  Gly  His  Lys  Ala  Tyr
     290                      295                      300

Leu  Cys  Gly  Pro  Pro  Ala  Met  Ile  Asp  Ala  Cys  Val  Thr  Thr  Leu  Ile
305                      310                      315                           320

Gln  Gly  Arg  Leu  Phe  Glu  Arg  Asp  Ile  Tyr  Phe  Glu  Lys  Phe  Ile  Ser
               325                      330                      335

Ala  Ala  Asp  Ala  Gln  Gln  Val  Arg  Ser  Pro  Leu  Phe  Lys  Arg  Val
               340                      345                      350
```

( 2 ) INFORMATION FOR SEQ ID NO:7:

( i ) SEQUENCE CHARACTERISTICS:
        ( A ) LENGTH: 37 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:7:

```
Phe  Val  Gln  Phe  Glu  Phe  Ser  Val  Gly  Thr  Pro  Glu  Leu  Cys  Val  Glu
1                   5                    10                       15

Leu  Met  Leu  Pro  Val  Ala  Ala  Phe  Glu  Glu  Phe  Cys  Leu  Ala  Gln  Lys
               20                   25                       30

Val  Thr  Arg  Leu  Asp
               35
```